US007273925B1

(12) United States Patent
Stahl et al.

(10) Patent No.: US 7,273,925 B1
(45) Date of Patent: Sep. 25, 2007

(54) METHODS AND PRODUCTS FOR REGULATING LECTIN COMPLEMENT PATHWAY ASSOCIATED COMPLEMENT ACTIVATION

(75) Inventors: Gregory L. Stahl, Clinton, MA (US); Charles D. Collard, Wellesley, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/464,303

(22) Filed: Dec. 15, 1999

Related U.S. Application Data

(60) Provisional application No. 60/112,390, filed on Dec. 15, 1998.

(51) Int. Cl.
*C12P 21/08* (2006.01)
*C07K 16/18* (2006.01)
*C12N 5/20* (2006.01)
*A61K 39/395* (2006.01)

(52) U.S. Cl. .......................... 530/387.3; 530/388.25; 530/389.3; 530/866; 435/325; 435/328; 435/337; 435/346; 424/133.1; 424/145.1; 424/809

(58) Field of Classification Search .......... 24/137.1; 514/2; 435/329, 325, 328, 337, 346; 424/133.1, 424/145.1, 809; 530/387.3, 388.25, 389.3, 530/866

See application file for complete search history.

(56) References Cited

U.S. PATENT DOCUMENTS 5,270,199 A * 12/1993 Ezekowitz
5,616,311 A    4/1997 Yen

FOREIGN PATENT DOCUMENTS

| JP | 06121695 | 5/1994 |
| JP | 07238100 | 9/1995 |
| WO | WO89/01519 A1 | 2/1989 |
| WO | WO90/08549 A1 | 8/1990 |
| WO | WO91/06010 A1 | 5/1991 |
| WO | WO93/18775 A1 | 9/1993 |
| WO | WO97/31121 A1 | 8/1997 |
| WO | WO99/39209 A1 | 8/1999 |
| WO | WO 00/35483 A1 | 6/2000 |
| WO | WO 01/12212 A1 | 2/2001 |

OTHER PUBLICATIONS

Janeway et al. Immunobiology, 3rd Edition, Garland Press, 1997, p. 13.8.*
Pierce Catalog (1995) p. T-19 and T-20 Pierce Corp.*
Janeway et al Immunobiology (1999) Fourth Edition Garland Press, p. 87.*
Abaza et a;. J. of Protein Chemistry, 11(5):433-444, (1992).*

Sato et al., Molecular characterization of a novel serine protease involved in activation of the complement system by mannose-binding protein. International Immunology. Apr. 1994, vol. 6, No. 4, pp. 665-669.
Endo et al., Exon structure of the gene encoding the hamanmannose-binding protein-associated serine protease light chain: comparison with complement C1r and C1s genes. International Immunology. Sep. 1996, vol. 8, No. 9, pp. 1355-1358.
Thiel, et al., A second serine protease associated with mannan-binding lectin that activates complement. Nature. Apr. 1997, vol. 386, pp. 506-510.
Endo et al., Two lineages of mannose-binding lectin-associated serine protease (MASP) in vertebrates, J. Immunology. Nov. 1998, vol. 161, pp. 4924-4930.
International Search Report—Intl. Appl. No., PCT/US99/29919—Dec. 15, 1999.
Amsterdam. E.A. et al., "Limitation of reperfusion injury by a monoclonal antibody to C5a during myocardial infarction in pigs", *Am J Physiol Heart Circ Physiol*, 1995, 268:H448-H457.
Endo, Y. et al., "Glomerular deposition of mannose-binding lectin (MBL) indicates a novel mechanism of complement activation in IgA nephropathy," *Nephrol Dial Transplant*, Aug. 1998, 13(8):1984-1990.
Jack, D.L. et al., Activation of complement by mannose-binding lectin on isogenic mutants of *Neisseria meningitidis* serogroup B, *J. Immunol*, Feb. 1998, 160(3):1346-53 Abstract Only
Vorup-Jensen, T. et al., "MASP-2, the C3 Convertase Generating Protease of the MBLectin Complement Activating Pathway", *Immunobiol.*, vol. 199, 1998, pp. 348-357.
Konami, Y. et al., "Correlation between carbohydrate-binding specificity and amino acid sequence of carbohydrate-binding regions of *Cytisus*-type anti-H(O) lectins", *FEBS Letters*, vol. 304, No. 2.3, pp. 129-135, Jun. 1992. .

(Continued)

*Primary Examiner*—Christina Chan
*Assistant Examiner*—F. Pierre VanderVegt
(74) *Attorney, Agent, or Firm*—Wolf, Greenfield & Sacks, P.C.

(57) ABSTRACT

The invention relates to methods and products for regulating lectin complement pathway associated complement activation. The methods include both in vitro and in vivo methods for inhibiting lectin complement pathway associated complement activation. The methods are accomplished by contacting a mammalian cell having surface exposed MBL ligand with an effective amount of a mannan binding lectin inhibitor to inhibit lectin complement pathway associated complement activation. The mannan binding lectin inhibitor may be administered to a subject to prevent cellular injury mediated by lectin complement pathway associated complement activation. The products of the invention include compositions of a mannan binding lectin inhibitor. The mannan binding lectin inhibitor is an isolated mannan binding lectin binding peptide that selectively binds to a human mannan binding lectin epitope and that inhibits lectin complement pathway associated complement activation. The products also include hybridoma cell lines and pharmaceutical compositions.

**9 Claims, 9 Drawing

OTHER PUBLICATIONS

Lennon, P.F. et al., "Complement-induced endothelial dysfunction in rabbits: mechanisms, recovery, and gender differences", *Am J Physiol Heart Circ Physiol*, 1996, 270:H1924-H1932.

Linder, E. et al., "Activation of complement by cytoskeletal intermediate filaments", *Nature*, vol. 278, Mar. 8, 1979, pp. 176-178.

Linder, E., "Antibody-independent Binding of C1q and Activation of Serium Complement by Human Skin in Vitro"< The Journal of Investigative Dermatology, vol. 78, No. 2, 1982, pp. 116-150.

Linder, E. et al., "Activation of Complement by Intermediate Filaments of Glomerular Epithelial Cells", *Clinical Immunology and Immunopathology*, vol. 40, 1986, pp. 265-275.

Shikhman, A.R. et al., "Cytokeratin Peptide SFGSGFGGGY Mimics N-Acetyl-β-D-Glucosamine in Reaction with Antibodies and Lectins, and Induces In Vivo and Anti-Carbonhydrate Antibody Response", *The Journal of Immunology*, 1994, pp. 5593-5606.

Super, M. et al., "The level of mannan-binding protein regulates the binding of complement-derived opsonins to mannan and zymosan at low serum concentrations," *Clin Exp Immunol.*, 1990, vol. 79, pp. 144-150.

Terai, I. et al., "Human serum mannose-binding lectin (MBL)-associated serine protease-1 (MASP-1): determination of levels in body fluids and identification of two forms in serum", *Clin Exp Immunol*, 1997, vol. 110, pp. 317-323.

Turner, M.W., "The lectin pathway of complement activation", Res Immunol, Feb. 1996, 147(2):110-5.

Vakeva, A.P. et al., "Myocardial Infarction and Apoptosis After Myocardial Ischemia and Reperfusion. Role of the Terminal Complement Components and Inhibition by Anti-C5 Therapy", *Circulation*, vol. 97, Jun. 9, 1998, pp. 2259-2267.

Agah, A. et al., "Isolation, Characterization, and Cloning of Porcine Complement Component C7", The Journal of Immunology, 2000, pp. 1059-1065, The American Association of Immunologists.

Collard, C.D. et al., "Reoxygenation of hypoxic human umbillical vein endothelial cells (HUVECs) activates the lectin complement pathway (LCP)", *FASEB Journal*, Mar. 17, 1998, p. 29A Abstract, vol. 12, No. 4, Meeting Info: Annual Meeting of Professional Research Scientists on Experimental Biology 98, Part 1, San Francisco, CA, USA, Apr. 18-22, 1998, Federation of American Societies of EX.

Collard, C.D. et al., "Hypoxia-induced expression of complement receptor type 1 (CR1, CD35) in human vascular endothelial cells", *AJP-Cell Physiology*, Feb. 1999, pp. C450-C458, vol. Issue 2.

Collard, C.D. et al., "Endothelial reoxygenation activates the lectin complement pathway: Inhibition with anti-human mannose binding lectin (MBL) therapy", *Molecular Immunology*, Mar.-Apr. 1999, p. 278 Abstract, vol. 36, No. 4-5, Meeting Info: 7th European Meeting on Complement in Human Disease, Helsinki, Finland, Jun. 17-20, 1999.

Collard, C.D. et al., "Complement activation following oxidative stress", *Molecular Immunology*, 1999, pp. 941-948, vol. 36, Elsevier Science Ltd.

Collard, C.D. et al., "Complement Activation after Oxydative Stress, Role of the Lectin Complement Pathway", *American Journal of Pathology*, May 2000, pp. 1549-1556, vol. 156, No. 5, American Society of Investigative Pathology.

Collard, C.D. et al., "Endothelial oxidative stress increases cytokeratin 1 (K1) expression and human mannose-binding (MBL) deposition", *Immunopharmacology*, Aug. 2000, p. 85, Abstract, vol. 49, No. 1-2, Print Meeting Info: XVIIITH International Complement Workshop, Salt Lake City, Utah, USA, Jul. 23-27, 2000.

Fitch, J.C.K. et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass", *Circulation*, Dec. 21/28, 1999, pp. 2499-2506, American Hearth Association.

Lhotta, K. et al., "Glomerular deposition of mannose-binding lectin in human glomerulonephritis", *Nephrology Dialysis Transplantation*, 1999, pp. 881-886, vol. 14, European Renal Association, European Dialysis and Transplant Association.

Linder, E., "Binding of C1q and Complement Activation by Vascular Endothelium", *The Journal of Immunology*, Feb. 1981, pp. 648-658, vol. 126 , No. 2.

Turner, M.W., "Mannose-binding lectin: the pluripotent molecular of the innate immune system", *Review Immunology Today*, Nov. 1996, pp. 532-540, vol. 17, No. 11.

Chaka, W. et al., "Induction of TNF-α in Human Perifpheral Blood Mononuclear Cells by the Mannoprotein of *Cryptococcus neoformans* Involves Human Mannose Binding Protein", *Journal of Immunology*, 1997, pp. 2979-2985, vol. 159, The Williams and Wilkins Co., Baltimore, USA.

Tenner, A.J. et al., "Mannose Binding Protein (MBP) Enhances Mononuclear Phagocyte Function via a Receptor that Contains the 126,000 $M_r$ Component of the C1q Receptors", *Immunity*, Oct. 1, 1995, pp. 485-493, vol. 3, No. 4, Cell Press USA.

Terai, I, et al., "$α_2$-Macroglobulin binds to and inhibits mannose-binding protein-associated serine protease", *International Immunology*, Oct. 1995, pp. 1579-1584, vol. 7, No. 10, Oxford University Press GB.

Agah et al., Isolation, cloning and functional characterization of porcine mannose-binding lectin. immunology. Mar. 2001;102(3):338-43.

Bhole et al., Therapeutic potential of targeting the complement cascade in critical care medicine. Crit Care Med. Jan. 2003;31(1 Suppl):S97-104. Review.

Blume et al., Activated endothelial cells elicit paracrine induction of epithelial chloride secretion. 6-Keto-PGF1alpha is an epithelial secretagogue. J Clin Invest. Sep. 15, 1998;102(6):1161-72.

Collard et al., Complement activation following reoxygeneration of hypoxic human endothelial cells: role of intracellular reactive oxygen species, NF-kappaB and new protein synthesis. Immunopharmacology. Mar. 1998;39(1):39-50.

Collard et al., Complement activation following oxidative stress. Mol Immunol. Sep.-Oct. 1999;36(13-14):941-8. Review.

Collard et al., Endothelial oxidative stress activates the lectin complement pathway: role of cytokeratin 1. Am J Pathol. Sep. 2001;159(3):1045-54.

Collard et al., Complement activation after oxidative stress: role of the lectin complement pathway. Am J Pathol. May 2000;156(5):1549-56.

Collard et al., Reoxygenation of hypoxic human umbilical vein endothelial cells activates the classic complement pathway. Circulation. Jul. 1, 1997;96(1):326-33.

Dahl et al., MASP-3 and its association with distinct complexes of the mannan-binding lectin complement activation pathway. Immunity. Jul. 2001;15(1):127-35.

Fiane et al., Mechanism of complement activation and its role in the inflammatory response after thoracoabdominal aortic aneurysm repair. Circulation. Aug. 19, 2003;108(7):849-56. Epub Aug. 4, 2003.

Hart et al., Initiation of complement activation following oxidative stress. In vitro and in vivo observations. Mol Immunol. Jun. 2004;41(2-3):165-71. Review.

Holt et al., Domain antibodies: proteins for therapy. Trends Biotechnol Nov. 2003;21(11):484-90. Review.

Igarashi et al., Specific binding of a synthetic peptide derived from an antibody complementarity determining region to phosphatidylserine. J Biochem (Tokyo). Feb. 1995;117(2):452-7.

Jordan et al., Inhibition of mannose-binding lectin reduces postischemic myocardial reperfusion injury. Circulation. Sep. 18, 2001;104(12):1413-8.

Kingman, Complement activation in myocardial infarction: A target for future treatments? Drug Discovery Today. 2000; 8: 313-4.

Lanzrein et al., Mannan-binding lectin in human serum, cerebrospinal fluid and brain tissue and its role in Alzheimer's disease. Neuroreport. May 11, 1998;9(7):1491-5.

Laune et al., Systematic exploration of the antigen binding activity of synthetic peptides isolated from the variable regions of immunoglobulins. J Biol Chem. Dec. 5, 1997;272(49):30937-44.

Lekowski et al., Ulex europaeus agglutinin II (UEA-II)is a novel, potent inhibitor of complement activation. Protein Sci. Feb. 2001;10(2):277-84.

Monnet et al., Synthetic peptides derived from the variable regions of an anti-CD4 monoclonal antibody bind to CD4 and inhibit HIV-1 promoter activation in virus-infected cells. J Biol Chem. Feb. 5, 1999;274(6):3789-96.

Montalto et al., A keratin peptide inhibits mannose-binding lectin. J Immunol. Mar. 15, 2001;166(6):4148-53.

Montalto et al., Role for complement in mediating intestinal nitric oxide synthase-2 and superoxide dismutase expression. Am J Physiol Gastrointest Liver Physiol. Jul. 2003;285(1):G197-206. Epub Mar. 13, 2003.

Rieben et al., Immunological M-enriched human intravenous immunoglobulin prevents complement activation in vitro and in vivo in a rat model of acute inflammation. Blood. Feb. 1, 1999;93(3):942-51.

Roos et al., Human IgA activated the complement system via the mannan-binding lectin pathway. J Immunol. Sep. 1, 2001;167(5):2861-8.

Roos et al., Therapeutic inhibition of the early phase of complement activation. Immunobiology. Sep. 2002;205(4-5);595-609. Review.

Roos et al., Functional characterization of the lectin pathway of complement in human serum. Mol Immunol. Jan. 2003;39(11):655-68.

Russell et al., Anti-inflammatory activity of human IgA antibodies and their Fab alpha fragments: inhibition of IgG-mediated complement activation. Eur J Immunol. Dec. 1989;19(12):2243-9.

Stahl, The Immune System—Complementary Medicine. The Economist. May 13, 2000; 26-7.

Stahl, New Inflammatory Pathway Discovered. Genetic Engineering News. May 15, 2000; 20(3):27-8.

Stahl et al., Reperfusion injury in surgery. Role of the endothelium, oxidative stress and complement activation (Invited review). New Surgery. 2001; 1:62-6.

Stahl et al., Role for the alternative complement pathway in ischemia/reperfusion injury. Am J Pathol. Feb. 2003;162(2):449-55.

Szebeni et al., Liposome-induced pulmonary hypertension: properties and mechanism of a complement-mediated pseudoallergic reaction. Am J Physiol Heart Circ Physiol. Sep. 2000;279(3):H1319-28.

Szebeni et al., Hemodynamic changes induced by liposomes and liposomes-encapsulated hemoglobin in pigs: a model for pseudoallergic cardiopulmonary reactions to liposomes. Role of complement and inhibition by soluble CT1 and anti-C5a antibody. Circulation. May 4, 1999;99(17):2302-9.

Taub et al., A monoclonal antibody against the platelet fibrinogen receptor contains a sequence that mimics a receptor recognition domain in fibrinogen. J Biol Chem. Jan. 5, 1989;264(1):259-65.

Tofukuji et al., Anti-C5a monoclonal antibody reduces cardiopulmonary bypass and cardioplegia-induced coronary endothelial dysfunction. J Thorac Cardiovasc Surg. Dec. 1998;116(6):1060-8.

Wallis et al., Localization of the serine protease-binding sites in the collagen-like domain of mannose-binding protein: indirect effects of naturally occurring mutations on protease binding and activation. J Biol Chem. Apr. 2, 2004;279(14):14065-73. Epub Jan. 14, 2004.

Walsh et al., Role of complement in myocardial ischemia and infarction. In: Szebeni J, editor. The Complement System. Novel Roles in Health and Disease. Kluwer Academic Publishers. Massachusetts, Jun. 2004.

Walsh et al., Myocardial Ischemia-reperfusion injury is dependent on lectin complement activation. American College of Cardiology. Mar. 10, 2004; 11:15am-11:30am (Presentation Abstract).

Zhao et al., Anoxia and reoxygenation of human endothelail cells decrease ceramide glucosyltranferase expression and activates caspases. FASEB J. Apr. 2003;17(6):723-4. Epub Feb. 5, 2003.

Zhao et al., Identification of human mannose binding lectin (MBL) recognition sites for novel inhibitory antibodies. Hybridoma and Hybridomics. Feb. 2002;21(1):25-36.

Zhao et al., Murine model of gastrointestinal ischemia associated with complement-dependent injury. J Appl Physiol. Jul. 2002;93(1):338-45.

Lekowski, R.W. et al., "Ulex europaeus Agglutinin II (UEA-II) is a Novel, Potent Inhibitor of Complement Activation on Human Endothelial Cells", Circulation, Nov. 2, 1999, vol. 110, No. 18 Suppl., p. 1.259, Meeting Info: 72nd Scientific Sessions of the American Heart Association, Atlanta, Georgia, USA, Nov. 7-10, 1999.

Office communication from USPTO, U.S. Appl. No. 09/638,420 mailed Jan. 14, 2003.

Office communication from USPTO, U.S. Appl. No. 09/638,420 mailed Oct. 21, 2003.

International Search Report PCT/US00/22123, mailed on Nov. 26, 2001.

Written Opinion, PCT/US00/22123, mailed on Sep. 27, 2001.

Written Opinion, PCT/US00/22123, mailed on Sep. 21, 2001.

Written Opinion, PCT/US00/22123, mailed on Mar. 30, 2001.

International Search Report PCT/US00/22123, mailed on Dec. 29, 2000.

Matsushita, M., et al. "Human mannose-binding protein is identical to a component of Ra-reactive factor", Biochemical and Biophysical Research Communications, vol. 183, No. 2, pp. 645-651, Mar. 16, 1992.

Collard CD, Büküsoglu C, Sperati CJ, Colgan SP, Stahl GL. Reoxygenation of hypoxic human umbilical vein endothelial cells (HUVECs) activates the classical complement (C) pathway, FASEB J. 1996; 10:A621—Abstract Only.

Väkevä AP, Collard CD, Büküsoglu C, Stahl GL. Complement regulation and activation following hypoxia and reoxygenation of human umbilical vein endothelial cells (HUVECs). FASEB J. 1996; 10:A622—Abstract Only.

Collard CD and Stahl GL. Deposition of the terminal complement complex (C5b-9) on human umbilical vein endothelial cells (HUVECs) following hypoxia and reoxygenation decreases intracellular levels of cyclic-guanosine monophosphate (cGMP). Circulation 1996; 94:1105—Abstract Only.

Agah A, Väkevä AP, Morse DS, Rollins SA and Stahl GL. Complement induced apoptosis in vitro and in vivo. Role of the terminal complement complex, C5b-9. Microcirculation 1997;4:124. —Abstract Only.

Collard CD and Stahl GL. Reoxygenation of hypoxic human umbilical vein endothelial cells (HUVECs) deposits C5b-9 and decreases intracellular cGMP. Microcirculation 1997;4:171—Abstract Only.

Väkevä AP, Morse DS, Rollins SA and Stahl GL. Reoxygenation of hypoxic human umbilical vein endothelial cells (HUVECs) activates complement and induces apoptosis. Role of C5b-9. Exp. Clin. Immunogenet. 1997;14:108—Abstract Only.

Agah A, Collard CD and Stahl GL. New protein synthesis and NF-κB translocation is required for complement activation on hypoxic/reoxygenated HUVECs. FASEB J. 1998; 12:A28. —Abstract Only.

Collard CD, Agah A, Morse DS, Rollins SA, Matis LA; Stahl GL. Reoxygenation of hypoxic HUVECs in human sera augments nuclear NF-κB translocation and expression of vascular cell adhesion molecule-1 (VCAM-1): Inhibition with anti-human C5 therapy. Molecular Immunology 1998; 35:335.—Abstract Only.

Szebeni J. Fontana JL, Wassef NM, Mongan PD, Morse DS, Stahl GL, Bunger R, Alving CR. Liposome-induced and complement-mediated cardiopulmonary distress in pigs as a model of pseudoallergic reactions to liposomal drugs. Molecular Immunology 1998; 35:401.—Abstract Only.

Szebeni J, Stahl GL, Fontana JL, Dobbins D, Mongan PD, Wassef NM, Morse DS, Bunger R, Alving CR. Liposome-induced acute cardiopulmonary distress in swine is mediated by complement. Circulation 1998; 98:1-133- Abstract Only.

Agah A, Young K and Stahl GL. Purification, characterization and CDNA sequencing of porcine mannose-binding lectin (MBL). FASEB J. 1999; 13:A284—Abstract Only.

Vakeva A, Collard CD, Laine P, Morse DS, Paavonen, Meri S, Kovanen, Stahl GL. Mannose-binding lectin co-localizes with complement in atherosclerotic human coronary arteries: a novel role for the lectin complement pathway in human cardiovascular disease. Molecular Immunology 1999; 36:302- Abstract Only.

Jordan JE, Morrissey M, Stahl GL. Anti-complement treatment protects hypoxic-reoxygenated HUVECs from apoptosis. Immunopharmacology 2000; 49:24- Abstract Only.

Zhao H, Stahl GL. Characterization of monoclonal antibodies (mAb) against native and recombinant human mannose-binding lectin (MBL). Immunopharmacology 2000; 49:83- Abstract Only.

Jordan JE and Stahl GL. Inhibition of mannose binding lectin reduces myocardial reperfusion injury: A role for the lectin complement pathway in cardiovascular disease. JACC 2001; 37:378A- Abstract Only.

Montalto MC Collard CD, Buras JA, Reenstra WR, Geis D, Rother RP, Stahl GL. A peptide mimic of N-acetyl-D glucosamine inhibits the lectin complement pathway following endothelial oxidative stress. FASEB J. 2001; 15:A339—Abstract Only.

Zhao H and Stahl GL. Epitope mapping monoclonal antibodies against human mannose binding lectin. FASEB J. 2001; 15:A685- Abstract Only.

Jordan JE, Montalto MC, Lopes de Rosa JR, Stahl GL. Regulation of pro-inflmmatory genes by the lectin complement pathway following myocardial ischemia-reperfusion. FASEB J. 2001; 15:A463—Abstract Only.

Jordan JE, Morrissey MA, Stahl GL. Isolation and characterization of anti-rat mannose binding lectin antibodies. FASEB J. 2001; 15:A338- Abstract Only.

Mary Walsh, Todd Bourcier, MinoruTakahashi and Gregory Stahl. Complement activation and tissue injury following myocardial ischemia and reperfusion is C1q independent. Molecular Immunology, 40: 215, 2003—Abstract Only.

Deepak Bhole, Todd Bourcier and Gregory Stahl. Anoxia/reoxygenation of rat cardiac myocytes precipitates complement activation. Molecular Immunology 40: 215, 2003—Abstract Only.

Melanie Hart, Kathleen Ceonzo, Jon Buras and Gregory Stahl. Gastrointestinal ischemia-reperfusion injury is complement-dependent but not dependent on C1q. Molecular Immunology 40: 187, 2003- Abstract Only.

Minoru Takahashi, Dayang Wu, Michelle Giannoni, Russell P. Rother, Gregory L. Stahl Cloning and characterization of recombinant human MASP-2 and the functionally blocking anti-human MBL monoclonal antibody, 3F8. Molecular Immunology 41: 314, 2004- Abstract Only.

M.C. Walsh, K. Takahashi, L. Shi , R. Rother, M. Bourgoun, S.D. Soloman, A. Ezekowitz, G.L. Stahl. Complement activation and tissue injury following myocardial ischemia and reperfusion is dependent on MBL. Molecular Immunology 41:322, 2004- Abstract Only.

* cited by examiner

METHODS AND PRODUCTS FOR REGULATING LECTIN COMPLEMENT PATHWAY ASSOCIATED COMPLEMENT ACTIVATION

RELATED APPLICATIONS

This application claims priority under 35 U.S.C. § 119 to U.S. Provisional Patent Application No. 60/112,390, filed Dec. 15, 1998, the entire contents of which is hereby incorporated by reference.

GOVERNMENT SUPPORT

The present invention was supported in part by grants from the National Institutes of Health HL56086, HL52886, and GM07592. The U.S. Government may retain certain rights in the invention.

FIELD OF THE INVENTION

The present invention relates to methods and products for regulating lectin complement pathway (LCP) associated complement activation. In particular, the invention relates to methods for inhibiting LCP associated complement activation by contacting a mammalian cell having a mannose binding lectin (MBL) ligand with an MBL inhibitor. The invention also relates to products which are MBL inhibitors, such as an MBL binding peptide.

BACKGROUND OF THE INVENTION

The immune system functions to defend the body against pathogenic bacteria, viruses and parasites. Immunity against foreign pathogens usually involves the complement system. The complement system is a cascade of 18 sequentially activated serum proteins which functions to recruit and activate other cells of the immune system, effect cytolysis of target cells and induce opsonization of foreign pathogens. Complement can be activated by the presence of either antibody/antigen complexes, as in the classical complement pathway, or microbial surfaces, as in the alternative complement pathway. Complement activation can also occur via the lectin complement pathway (LCP). Lectins are carbohydrate-binding proteins that recognize oligosaccharide structures present on cell surfaces, the extracellular matrix, and secreted glycoproteins. As shown in FIG. 1, these distinct activation pathways ultimately converge at the common enzymatic step of serum protein C3 cleavage to C3b and C3a. This in turn initiates the terminal steps of complement function including the cleavage of C5 to C5b and C5a and subsequent deposition of C5b-C9 onto the target cell membrane.

The LCP is an antibody-independent cascade that is initiated by binding of mannan-(or mannose) binding lectin (MBL) to cell surface carbohydrates on bacteria, yeasts, parasitic protozoa, and viruses (Turner MW, "Mannose-binding lectin: The pluripotent molecule of the innate immune system", *Immunol. Today,* 1996;17:532-540). MBL (≈p600 kDa) is a member of the collectin protein family and is structurally related to the classical complement C1 subcomponent, C1q. Associated with MBL are two serine proteases, Mannose binding lectin associated serine protease, MASP-1 and MASP-2, which show in striking homology to the two C1q-associated serine proteases of the classical complement pathway, C1r and C1s (Thiel S, et al., "A second serine protease associated with mannan-binding lectin that activates complement", *Nature* 1997;386:506-510). The selectivity of MBL sugar binding is: N-acetyl-D-glucosamine (GluNAc)>mannose>N-acetylmannosamine and fucose>maltose>glucose>>galactose and N-acetylgalactosamine (Thiel S, et al., "A second serine protease associated with mannan-binding lectin that activates complement", *Nature* 1997;386:506-510; Turner M W, "Mannose-binding lectin: The pluripotent molecule of the innate immune system", *Immunol. Today,* 1996;17:532-540). Binding of the MBL/MASP complex to cell surface carbohydrates activates the LCP, which in turn activates the classical complement pathway independently of C1q, C1r, C1s or antibodies (FIG. 1). Most if not all the carbohydrate moieties to which MBL binds are not normally expressed by unperturbed human tissue.

SUMMARY OF THE INVENTION

The present invention relates to methods and products for regulating lectin complement pathway (LCP) associated complement activation. Prior to the instant invention, it was known that LCP associated complement activation was a mechanism used by the body to recognize and destroy an invading microorganism. LCP activation normally occurs through the binding of mannan-binding lectin (MBL) and its two associated serine proteases, MASP-1 and MASP-2, to carbohydrates on the surface of microorganisms. Once MBL and MASP-1 and MASP-2 are localized to the surface of the microorganism, complement begins to assemble, ultimately killing the microorganism. These prior art teachings demonstrate that MBL is an important cellular component in the process of the eradication of infectious microorganisms. In fact, MBL deficiencies can result in medical disorders. A disease known as MBL deficiency, in which children are deficient in MBL, renders the children prone to the development of infectious diseases.

The present invention is based upon the surprising discovery that MBL recognizes specific carbohydrates or peptides on the surface of mammalian endothelial cells, causing complement deposition through activation of the LCP. According to U.S. Pat. No. 5,270,199 issued to Ecekowitz, MBL does not recognize the cell wall of human and animal cells. In contrast to these prior art teachings, it has been discovered, according to the invention, that MBL does recognize specific sequences on the surface of mammalian cells. It has also been discovered that MBL deposition on the surface of mammalian cells results in activation of LCP, contributing to the development of diseased or damaged tissue.

In one aspect, the invention is a method for inhibiting LCP-associated complement activation. The method includes the step of contacting a mammalian cell having a surface exposed MBL ligand with an effective amount of an MBL inhibitor to inhibit cellular MBL deposition and LCP-associated complement activation. In one illustrative embodiment, the method is an in vitro screening assay.

In another aspect, the invention is a method for inhibiting a cellular injury mediated by LCP-associated complement activation. The method includes the step of administering to a subject in need thereof an effective amount of an MBL inhibitor to inhibit LCP-associated complement activation.

In one embodiment of the methods of the invention, the MBL inhibitor is an isolated MBL binding peptide. In an illustrative embodiment, the isolated MBL binding peptide has an MBL binding CDR3 region or functional variant thereof. In some embodiments, the isolated MBL binding peptide is an antibody fragment. In other embodiments, the isolated MBL binding peptide is an antibody.

According to another embodiment of the methods of the invention, the MBL inhibitor is an isolated MASP binding peptide. The isolated MASP binding peptide may bind to either MASP-1 or MASP-2 or both, preventing MASP from participating in the LCP.

The cellular injury mediated by LCP-associated complement activation may contribute to the development of injured tissue associated with a variety of disorders. In one embodiment, the cellular injury is associated with atherosclerosis. In another embodiment, the cellular injury is associated with arthritis, myocardial infarction, ischemia and reperfusion, transplantation, CPB, stroke, ARDS, SLE, Lupus, or dialysis.

The MBL inhibitor may be administered to the subject by any route known in the art. When the cellular injury is associated with the pulmonary system, the MBL inhibitor may be administered to the subject by an aerosol route of delivery.

According to another aspect of the invention, an MBL inhibitor is provided. The MBL inhibitor is an isolated peptide that selectively binds to a human MBL epitope and inhibits LCP-associated complement activation.

In another aspect, the invention is a hybridoma cell line. In one illustrative embodiment, the hybridoma cell line is the cell line deposited under ATCC accession number HB-12621. In another embodiment, the hybridoma cell line is the cell line deposited under ATCC accession number HB-12620. In another embodiment, the hybridoma cell line is the cell line deposited under ATCC accession number HB-12619.

According to yet another aspect, the invention is a composition of an MBL inhibitor, wherein the MBL inhibitor is an isolated binding peptide that selectively binds to a human MBL epitope and that inhibits LCP-associated complement activation. In an illustrative embodiment the composition is a pharmaceutical composition including an effective amount for treating an MBL mediated disorder of the isolated MBL binding peptide and a pharmaceutically acceptable carrier. In one embodiment, the composition also includes a drug for the treatment of an MBL mediated disorder.

In one embodiment the isolated MBL binding peptide has an MBL binding $CDR3_1$ region or a functional variant thereof of a monoclonal antibody produced by hybridoma cell line $_{3F8}$ deposited under ATCC accession number HB-12621. In another embodiment the isolated MBL binding peptide has an MBL binding $CDR3_2$ region or a functional variant thereof of a monoclonal antibody produced by hybridoma cell line $_{२49}$ deposited under ATCC accession number HB-12620. In another embodiment the isolated MBL binding peptide has an MBL binding $CDR3_2$ region or a functional variant thereof of a monoclonal antibody produced by hybridoma cell line $_{hMBL1.2}$ deposited under ATCC accession number HB-12619.

The isolated peptide may be an intact soluble monoclonal antibody. In one embodiment the isolated peptide is monoclonal antibody (3F8) produced by the hybridoma cell line deposited under ATCC Accession No. HB-12621. In another embodiment the isolated peptide is monoclonal antibody $_{(2A9)}$ produced by the hybridoma cell line deposited under ATCC Accession No. HB-12620. In another embodiment the isolated peptide is monoclonal antibody $_{hMBL1.2}$ produced by the hybridoma cell line deposited under ATCC Accession No. HB-12619. In an illustrative embodiment the isolated peptide is a humanized monoclonal antibody.

According to some embodiments the isolated peptide is an antibody fragment. The isolated peptide, for instance, may be a monoclonal antibody fragment selected from the group consisting of an $F(ab')_2$ fragment, Fd fragment, and an Fab fragment. The isolated peptide may also be a peptide having a light chain CDR2 region selected from the group consisting of a $CDR2_{(3F8)}$ of a monoclonal antibody produced by hybridoma$_{(3F8)}$ deposited under ATCC Accession No. HB-12621, a $CDR2_{(2A9)}$ of a monoclonal antibody produced by hybridoma $_{2A9}$ deposited under ATCC Accession No. HB-12620, and a $CDR2_{(hMBL1.2)}$ of a monoclonal antibody produced by hybridoma$_{(hMBL1.2)}$ deposited under ATCC Accession No. HB-12619. In another embodiment the isolated peptide has a light chain CDR1 region selected from the group consisting of a $CDR1_{(3F8)}$ of a monoclonal antibody produced by hybridoma$_{(3F8)}$ deposited under ATCC Accession No. HB-12621, a $CDR1_{(2A9)}$ of a monoclonal antibody produced by hybridoma$_{(2A9)}$ deposited under ATCC Accession No. HB-12620, and a $CDR1_{(hMBL1.2)}$ of a monoclonal antibody produced by hybridoma$_{(hMBLA2)}$ deposited under ATCC Accession No. HB-12619.

In another aspect, the invention is a composition, wherein the MBL inhibitor is an anti-MBL antibody that: (i) selectively binds to a human MBL epitope, and (ii) prevents LCP activation.

In yet another aspect, the invention is a method for screening a subject for susceptibility to treatment with an MBL inhibitor. The method includes the steps of isolating a mammalian cell from a subject, and detecting the presence of an MBL on a surface of the mammalian cell, wherein the presence of the MBL indicates that the cell is susceptible to LCP-associated complement activation and that the subject is susceptible to treatment with an MBL inhibitor. In one embodiment, the method includes the step of contacting the MBL with a detection reagent that selectively binds to the MBL to detect the presence of the MBL. The detection reagent in one embodiment is an isolated MBL binding peptide.

A method for screening a subject for susceptibility to treatment with MBL inhibitor is provided in another aspect of the invention. The method includes the steps of contacting a mammalian cell from a subject with a labeled isolated MBL binding peptide, and detecting the presence of an MBL on the surface of the mammalian cell, wherein the presence of the MBL indicates that the cell is susceptible to LCP-associated complement activation and that the subject is susceptible to treatment with an MBL inhibitor. In one embodiment, the mammalian cell is an endothelial cell.

Each of the limitations of the invention can encompass various embodiments of the invention. It is, therefore, anticipated that each of the limitations of the invention involving any one element or combinations of elements can be included in each aspect of the invention.

Figure 3:
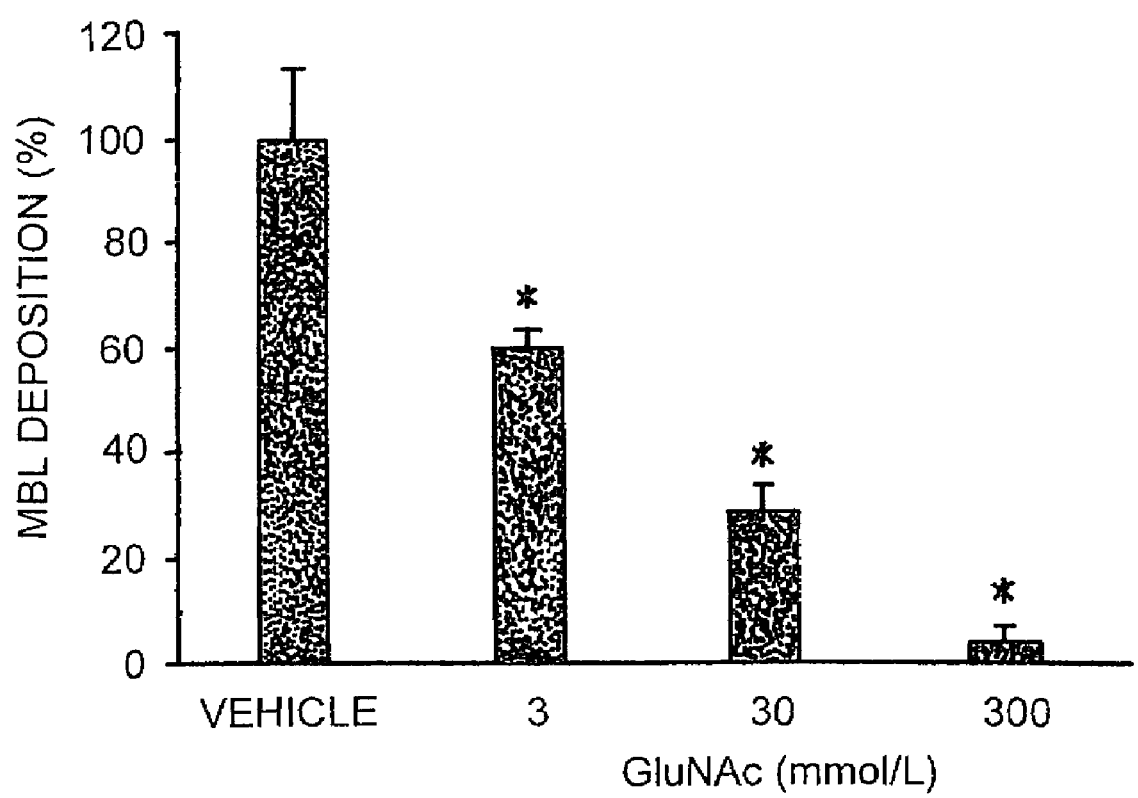

FIG. 3 is a graph depicting MBL deposition on HUVECs (ELISA). MBL deposition on HUVECs subjected to zero (normoxia) or 24 hours of hypoxia followed by 3 hours of reoxygenation was examined by ELISA using a monoclonal anti-human MBL antibody. MBL deposition on hypoxic HUVECs reoxygenated in the presence of 30% human serum (vehicle) was significantly greater than normoxic HUVECs or hypoxic HUVECs reoxygenated in 30% human serum treated with 30 mmol/L GluNac.

Figure 4A:
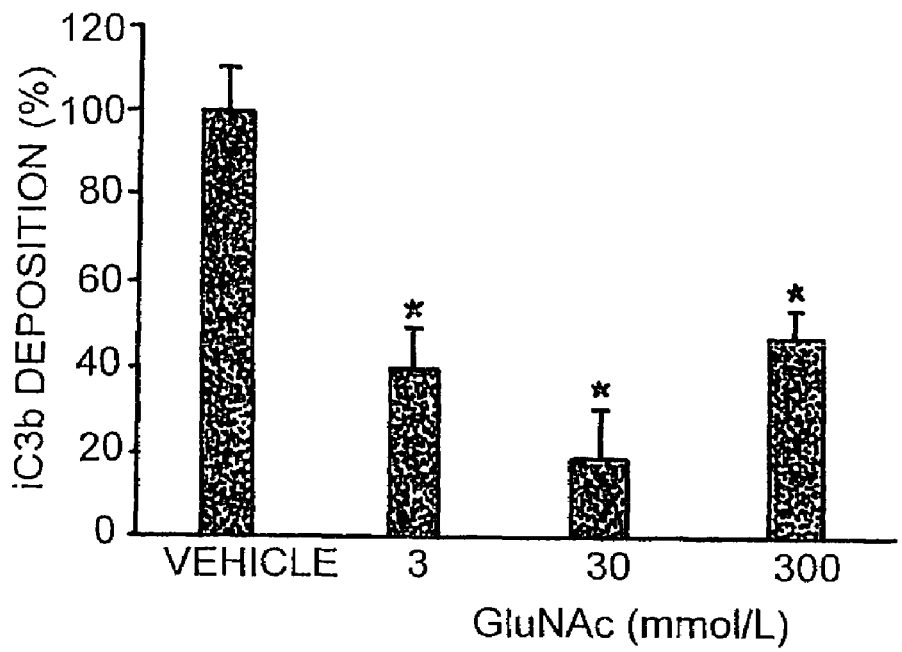

FIG. 4a is a graph depicting iC3b deposition following competitive inhibition of MBL. iC3b deposition was studied by ELISA on HUVECs reoxygenated in the presence of 30% human serum treated with 30 mmol/L GluNAc, D-mannose, or L-mannose. Deposition of iC3b on hypoxic HUVECs reoxygenated in 30% human serum (vehicle) or 30% human serum treated with L-mannose was significantly greater than normoxic HUVECs. iC3b deposition, however, on HUVECs reoxygenated in 30% human serum treated with GluNAc or D-mannose did not significantly differ from normoxic controls.

Figure 4B:
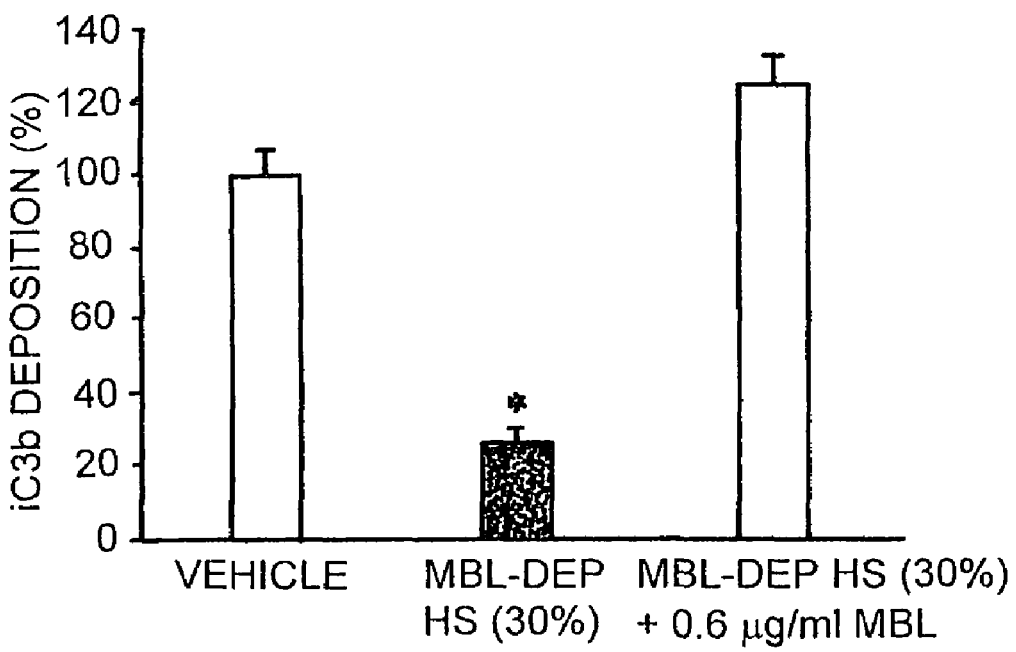

FIG. 4b is a graph depicting iC3b deposition following depletion of MBL from human serum. HUVECs were reoxygenated in the presence of MBL-depleted human serum to inhibit the lectin complement pathway. Deposition of iC3b (ELISA) on hypoxic HUVECs reoxygenated in 30% human serum was significantly greater ($p<0.05$) than normoxic HUVECs. iC3b deposition, however, on hypoxic HUVECs reoxygenated in 30% MBL-depleted human cell was significantly less ($p<0.05$) than hypoxic HUVECs reoxygenated in 30% human serum. When MBL was added back to the MBL-depleted human serum, iC3b deposition on the hypoxic/reoxygenated HUVECs was significantly greater than normoxic HUVECs.

Figure 5:
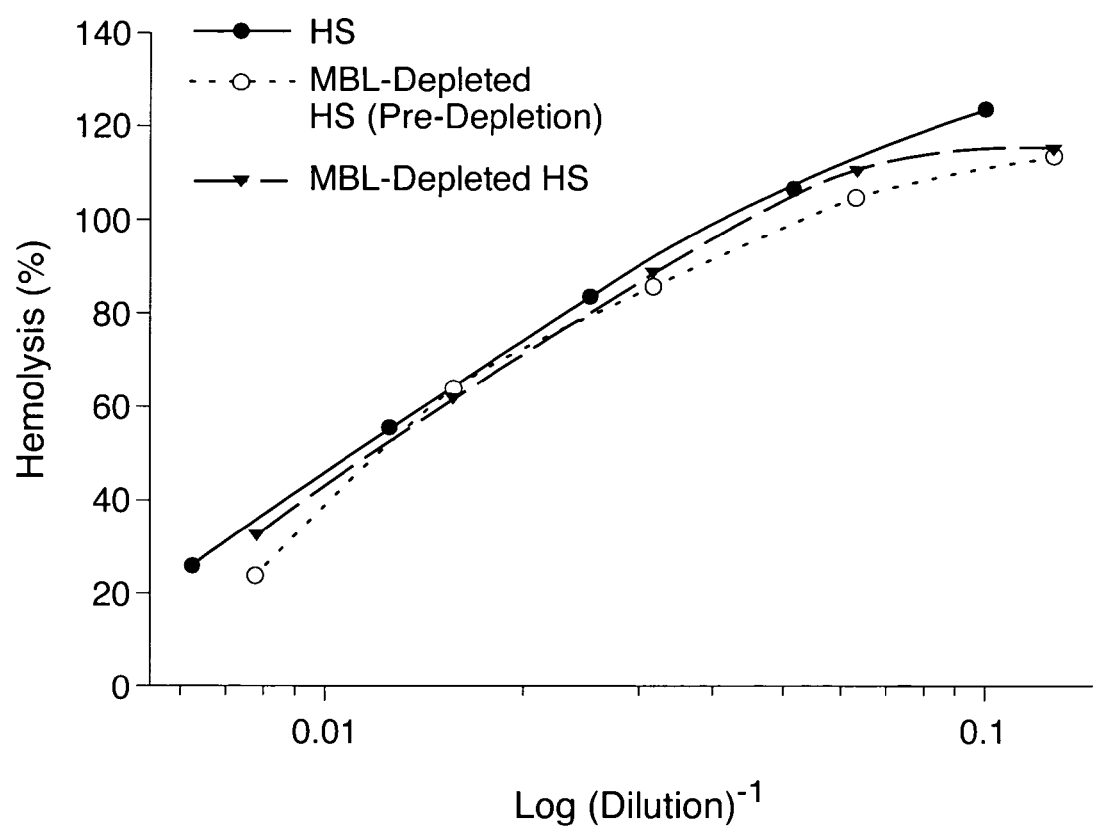
Figure 6:
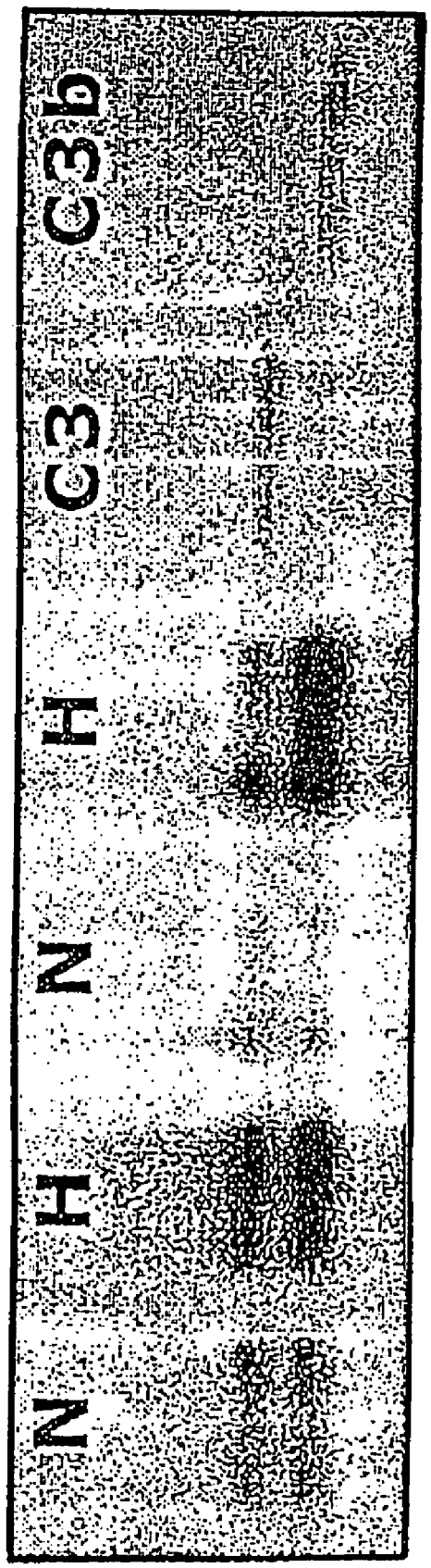

FIG. 5 is a graph depicting percent hemolysis as an indicator of classical complement pathway activity. No significant differences in the serum complement hemolytic assay ($CH_{50}$) were observed between human serum or MBL-depleted human serum, indicating that depletion of MBL did not inhibit or deplete classical complement pathway activity;

FIG. 6 depicts a Western blot analysis of C3 activation following hypoxia/reoxygenation using purified C2, C3, C4, and MBL. Western blot analysis of the C3 and C3b α'-chain was performed under reduced conditions with a polyclonal anti-human C3 antibody on the supernatants of normoxic and hypoxic (12 hours) HUVECs reoxygenated for 3 hours in the presence of purified C2, C3, C4, and MBL. Lanes 1 and 2 represent normoxic HUVECs supernatant, lanes 3 and 4, hypoxic HUVECs supernatant, lane 5, purified C3 standard, and lane 6, purified C3b standard. The results demonstrate an increased band density of C3b α'-chain in the hypoxic/reoxygenated supernatants compared to the normoxic supernatants. The Figure is representative of five experiments.

Figure 7:
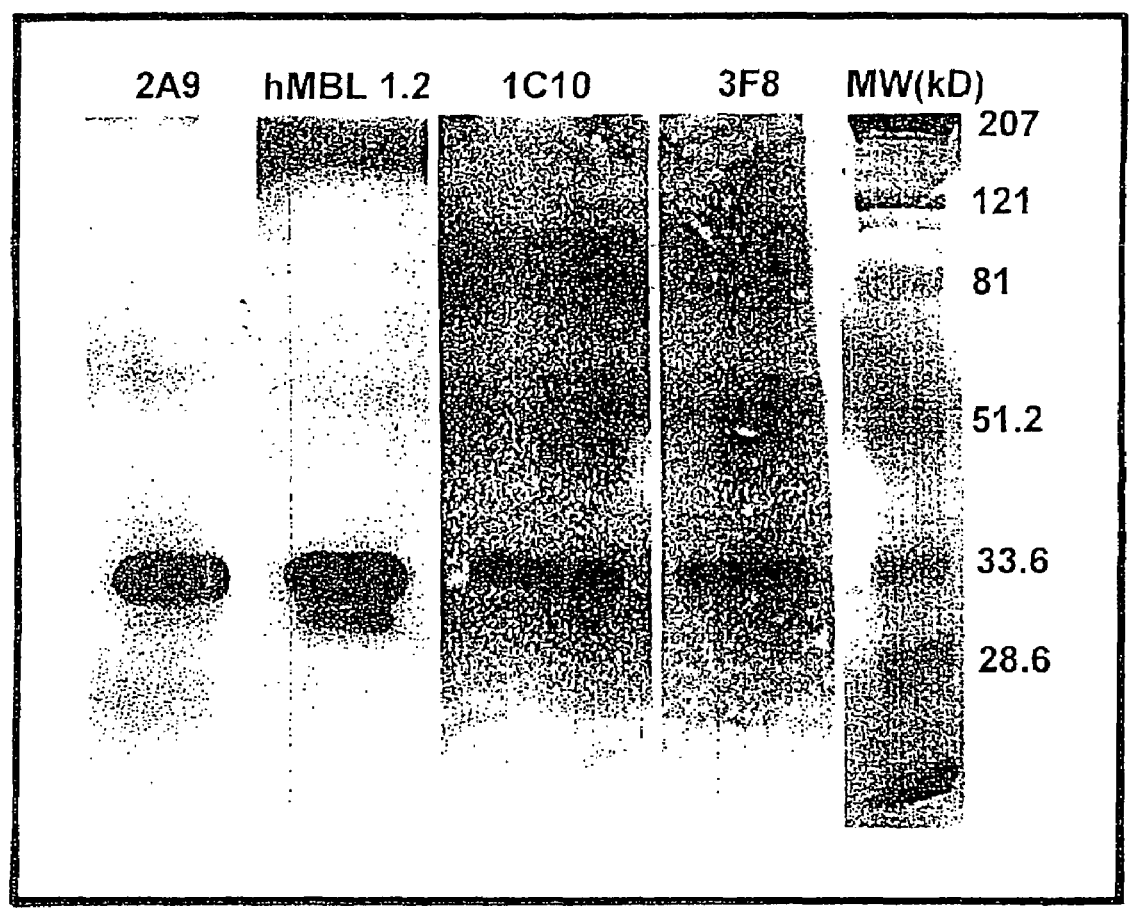

FIG. 7 is a scan of a Western blot analysis of human MBL. Monoclonal antibodies 3F8, hMBL1.2, 2A9 or 1C10 were used for western blot analysis of reduced MBL. Lanes 1, 2, 3 and 4 represent staining of reduced human MBL with 10 μg/ml of mAb 2A9, hMBL1.2, 1C10 or 3F8, respectively. A single band with an approximate molecular weight (MW) of 32 kDa (i.e., consistent with MBL) was observed with each mAb. This figure is representative of three separate experiments.

Figure 8:
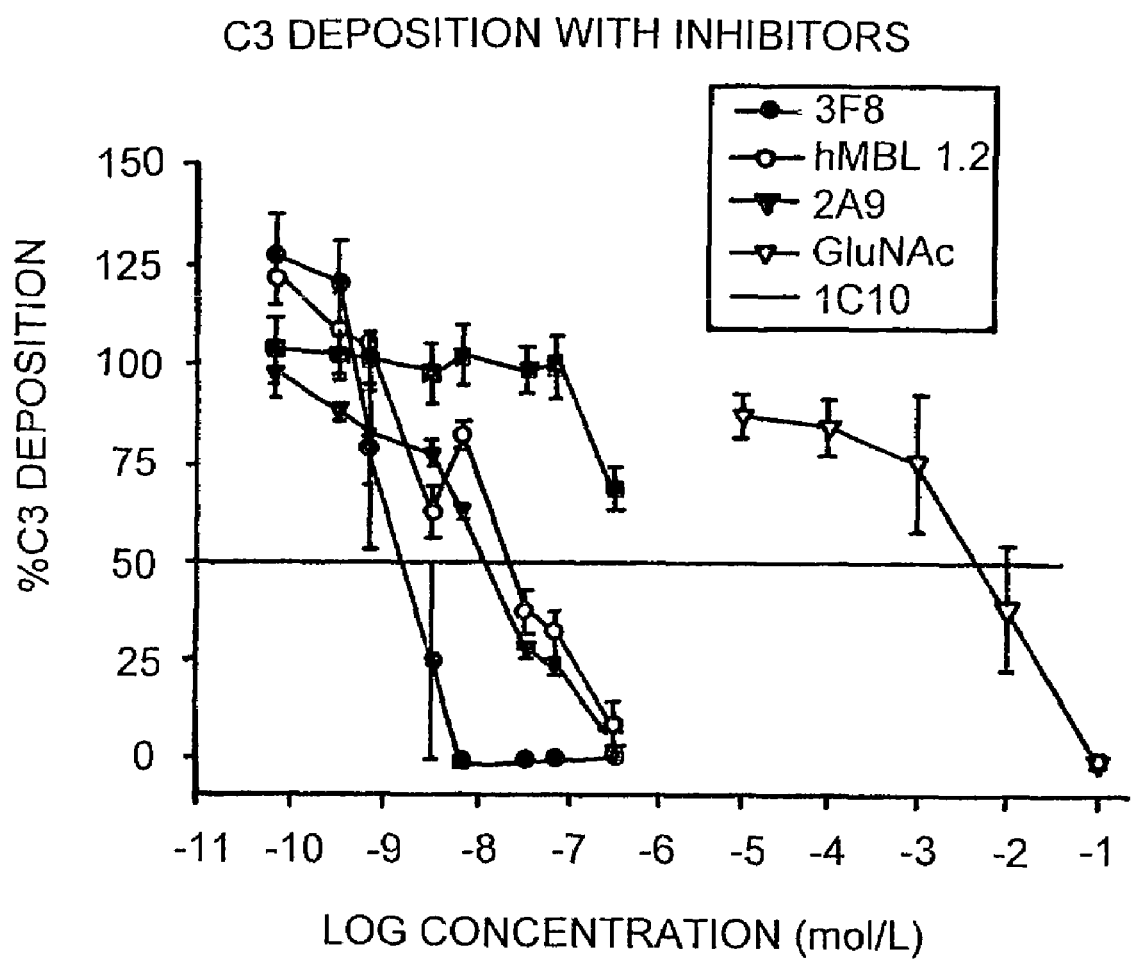

FIG. 8 is a graph depicting C3 deposition with inhibitors.

Figure 9:
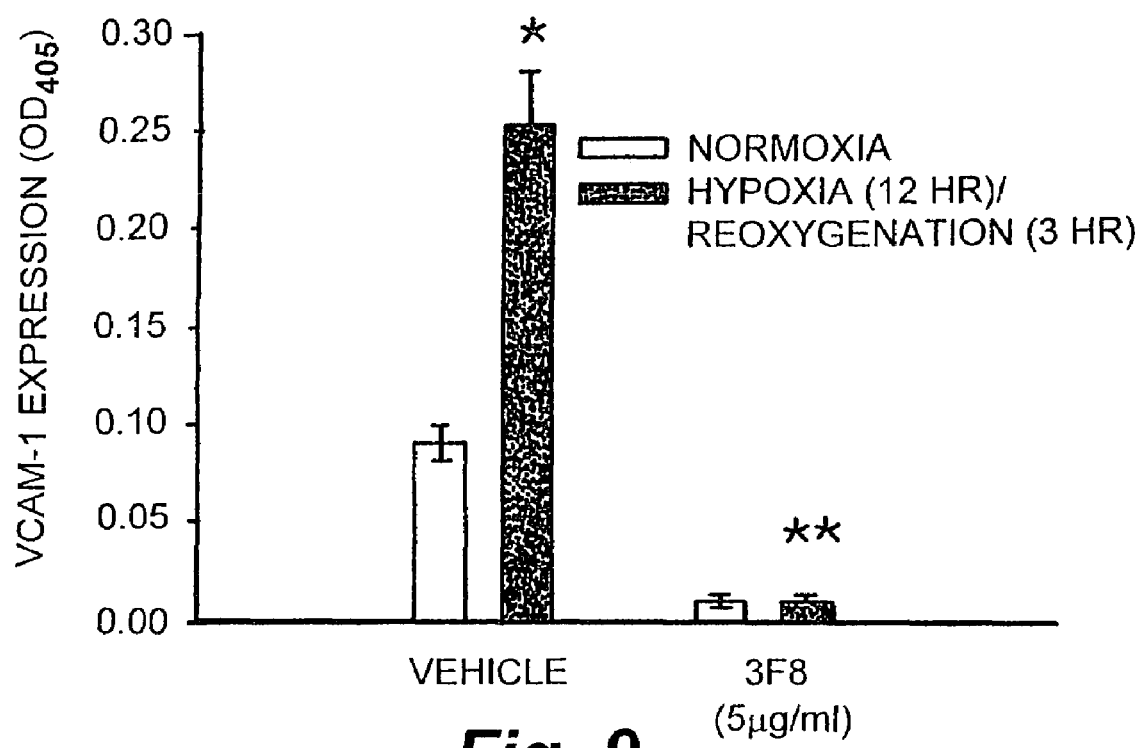

FIG. 9 is a graph depicting inhibition of VCAM-1 expression. Reoxygenation of hypoxic HUVECs in 30% HlS treated with PBS (Vehicle) induced a significant increase in VCAM-1 expression compared to normoxic cells incubated with 30% HS. Treatment of the 30% HS with 3F8 (5 μg/ml) significantly inhibited VCAM-1 expression. The bars represent the mean of 3 individual experiments. Brackets represent SEM. * represent $p<0.05$ is compared to the respective normoxia control. ** represent $p<0.05$ compared to vehicle treated hypoxia group.

DETAILED DESCRIPTION OF THE INVENTION

The invention relates to methods and products for regulating and manipulating lectin complement pathway (LCP)-associated complement activation. As discussed above, the invention is based on the finding that LCP-associated complement activation plays a role in complement induced cellular injury of mammalian cells. It was discovered according to the invention that MBL interacts with carbohydrates or peptides on the surface of mammalian cells in vitro and in vivo. The surface associated MBL leads to the accumulation of complement on the surface of the cell, ultimately leading to cell injury or death. According to the prior art, LCP-associated complement activation was predominantly associated with infectious microorganisms, suggesting that MBL deposition should be promoted in order to enhance the killing of infectious microorganisms. It was discovered, according to the invention, that in mammals it is preferable to block MBL cellular association, preventing LCP-associated complement activation rather than to promote it. The LCP is not necessary for eradication of infectious microorganisms in adult mammals, and in fact, it contributes to cellular injury associated with several types of disorders, such as atherosclerosis, arthritis, myocardial infarction, ischemia and reperfusion, transplantation, CPB, stroke, ARDS, SLE, Lupus, or dialysis.

In one aspect, the invention is a method for inhibiting LCP-associated complement activation. The method includes the steps of contacting a mammalian cell having surface exposed MBL ligand with an effective amount of an MBL inhibitor to inhibit LCP-associated complement activation.

The methods of the invention are useful for inhibiting LCP-associated complement activation on the surface of a mammalian cell having surface exposed MBL ligand (carbohydrate or peptide groups) recognized by MBL. The mammalian cell may be any cell in which the cell surface carbohydrates or peptides interact with MBL. In one illustrative embodiment, the mammalian cell is an endothelial cell having a surface exposed MBL ligand. For instance, vascular endothelial cells have been shown in subjects that have sustained ischemic/reperfusion injury to express an MBL ligand. Mammalian cells having MBL ligands can easily be identified. For instance, an MBL binding assay (e.g., such as those described below) can be used to identify MBL ligands.

The method for inhibiting LCP-associated complement activation may be used for a variety of in vitro and in vivo purposes. The method may be used, for instance, as an in vitro screening assay. The in vitro screening assay may be used to identify compounds which function as an MBL inhibitor, such as the assay described above, to identify mammalian cells having surface exposed MBL ligands, or to detect susceptibility of a subject to treatment with MBL inhibitor. In order to screen a subject for susceptibility to treatment with an MBL inhibitor, a cell is isolated from the subject and the presence of MBL or the ability of MBL to bind to the surface is detected. If MBL is present on the surface of a cell or is able to bind to the surface of a cell, then the cell is susceptible to LCP-associated complement activation. If this is the case, then the subject is susceptible to treatment with an MBL inhibitor.

The methods of the invention are also useful in vivo when it is desirable to inhibit MBL deposition on a mammalian cell surface. For instance, the methods of the invention are useful for treating an MBL mediated disorder. The MBL inhibitors can be used alone as a primary therapy or in combination with other therapeutics as an adjuvant therapy to enhance the therapeutic benefits of other medical treatments.

The mammalian cell is contacted with an MBL inhibitor. The step of "contacting" as used herein refers to the addition of the MBL inhibitor to a medium containing a mammalian cell. The medium may be an in vitro tissue culture or a biological specimen, an ex vivo sample, or in vivo. The step of contacting refers to the addition of the MBL inhibitor in such a manner that it will prevent LCP-associated complement activation associated with the mammalian cell.

An "MBL mediated disorder" as used herein is a disorder which involves cellular injury caused by LCP-associated complement activation. MBL disorders include, for instance, atherosclerosis, arthritis, myocardial infarction, ischemia and reperfusion, transplantation, CPB, stroke, ARDS, SLE, Lupus, or dialysis. Each of these disorders is well-known in the art and is described, for instance, in *Harrison's Principles of Internal Medicine* (McGraw Hill, Inc., New York).

Atherosclerosis and myocardial infarction can lead to ischemia-reperfusion (I/R) injury. One of the underlying mechanisms for I/R-induced injury is the hypoxic and reoxygenated environments created in affected tissues. Fluctuations in oxygen content as observed in these instances can create oxygen free radicals which have been reported to, among other things, modulate endothelial cell surface profile.

The invention also is useful for treating cellular injury arising from ischemia/reperfusion associated with atherosclerosis and/or cardiovascular remodeling. Injury to the vascular system can lead to a number of undesirable health conditions, including, for example, forms of atherosclerosis and arteriosclerosis that are associated with unwanted vascular smooth muscle cell proliferation. A common injury to the vascular system occurs as a side effect of a medical procedure for treating ischemic heart disease. Ischemia refers to a lack of oxygen due to inadequate perfusion of blood. Ischemic heart disease is characterized by a disturbance in cardiac function due to an inadequate supply of oxygen to the heart. The most common form of this disease involves a reduction in the lumen of coronary arteries, which limits coronary blood-flow. Under these conditions the carbohydrate or peptide residues of the cell surface become exposed or an MBL ligand is synthesized, allowing MBL to associate with the cell surface and initiate the LCP associated complement activation.

When ischemic heart disease becomes very serious, then management must be invasive. Until recently, ischemic heart disease was treated by coronary-artery, bypass surgery. Less invasive procedures, however, now have been developed. These procedures involve the use of catheters introduced into the narrowed region of the blood vessel ("the stenosis") for mechanically disrupting, laser ablating or dilating the stenosis.

The compositions may be administered in combination with other therapeutic treatments. The most widely used method to achieve revascularization of a coronary artery is percutaneous transluminal coronary angioplasty. A flexible guide wire is advanced into a coronary artery and positioned across the stenosis. A balloon catheter then is advanced over the guide wire until the balloon is positioned across the stenosis. The balloon then is repeatedly inflated until the stenosis is substantially eliminated. This procedure, as compared to heart surgery, is relatively noninvasive and can result in hospital stays of only three days. The procedure is an important tool in the management of serious heart conditions.

An "MBL inhibitor" as used herein is a compound that prevents LCP-associated complement activation. The MBL inhibitor may function by blocking MBL deposition on the surface of a mammalian cell or by blocking the association of MASP-1 or MASP-2 or C3b associated with MBL deposition. The ability of an MBL inhibitor to block MBL deposition or prevent association of MASP-1, MASP-2, or C3b with MBL can be detected using routine in vitro binding assays, such as the following assay (also described in the Examples).

MBL deposition (or association with MASP-1, MASP-2, or C3b) can be measured by ELISA on normoxic HUVECs and HUVECs subjected to 24 hr of hypoxia followed by 3 hr of reoxygenation in the presence of 30% human serum (HS) or 30% HS treated with 3, 30, or 300 mmol/L of N-acetyl-D-glucosamine (GluNAc) or with the putative binding peptide to inhibit competitively MBL deposition.

C3 and MBL specific cell surface ELISAs can be performed using peroxidase-conjugated polyclonal goat anti-human C3 antibody (Cappel, West Chester, Pa.) and monoclonal anti-human MBL antibody (Biodesign, Kennebunk, Me., clone #131-1), respectively. HUVECs are grown to confluence on 0.1% gelatinized 96-well plastic plates (Corning Costar, Cambridge, Mass.). The plates are then subjected to 0 (normoxia) or 24 hr of hypoxia. Hypoxic stress is maintained using a humidified sealed chamber (Coy Laboratory Products, Inc., Grass Lake, Mich.) at 37° C. gassed with 1% $O_2$, 5% $CO_2$, balance $N_2$ (Collard C D, et al., "Reoxygenation of hypoxic human umbilical vein endothelial cells activates the classical complement pathway", *Circulation,* 1997;96:326-333). Following the specified period of normoxia or hypoxia, the cell media are aspirated and 100 µl of one the following is added to each well: 1) 30% HS, 2) Hank's balanced salt solution, 3) 30% HS +3, 30, or 300 mmol/L GluNAc, 4) 30% HS+3, 30, or 300 mmol/L D-mannose, 5) 30% HS+3, 30, 300 mmol/L L-mannose, 6) 30% MBL-depleted HS 7) 30% MBL-depleted HS+0.6 µg/ml MBL or 8) 30% HS+3, 30, or 300 mmol/L putative MBL binding peptide. Additionally, 100 µl of purified MBL (3-300 ng/ml) is added to select wells to form a standard curve for quantitative analysis of MBL deposition. The cells are then reoxygenated for 3 hr at 37° C. in 95% air and 5% $CO_2$. The cells are washed and then fixed with 1% paraformaldehyde (Sigma Chemical Co., St. Louis, Mo.) for 30 min. The cells are then washed and incubated at 4° C. for 1.5 hr with 50 µl of peroxidase-conjugated polyclonal goat anti-human C3 antibody (1:1000 dilution) or monoclonal anti-human MBL antibody (1:1000 dilution). The MBL ELISA plates are then washed and incubated for 1 hr at 4° C. with 50 µl of peroxidase-conjugated polyclonal goat anti-mouse IgG secondary antibody (1:1000 dilution). After washing the cells, the plates are developed with 50 µl of ABTS (2,2'-azino-bis(3-ethylbenzthiazoline-6-sulfonic acid)), and read (Molecular Devices, Sunnyvale, Calif.) at 405 nm. Background controls for the C3 ELISA consist of cells to which only the anti-human C3 antibody is added (i.e., no HS) or cells incubated with 30% heat-inactivated HS. Background controls for the MBL ELISA consist of cells to which only secondary antibody and an isotype control monoclonal antibody to porcine C5a are added. Background optical density is subtracted from all groups. ELISA experiments are generally performed 3 times using 6 wells per experimental group. Endothelial C3 and MBL deposition on normoxic vs. hypoxic HUVECs is analyzed by two-way analysis of variance (ANOVA).

The MBL inhibitor prevents LCP-associated complement activation. Whether a particular compound can inhibit LCP-associated complement activation can also be assessed using routine in vitro screening assays. For instance, the Complement hemolytic assay ($CH_{50}$) described in the Examples below can be performed on MBL-depleted HS in order to demonstrate that MBL depletion inhibit LCP-associated complement activation. The assay may be performed, however, using MBL containing HS and adding an MBL binding peptide and/or a control peptide.

In one illustrative embodiment, the MBL inhibitor is an isolated MBL binding peptide. An "isolated MBL binding peptide" as used herein is a peptide which binds to MBL and inhibits LCP associated complement activation. One method by which MBL binding peptides inhibit LCP associated complement activation is by binding to MBL and inhibiting MBL association with surface exposed MBL ligands. Additionally, the MBL binding peptide may bind to MBL and inhibit the association between MBL and MASP-1 or −2 and/or C3b. Several peptides which bind to MBL or MASP have been described in the art, including Lanzrein, A. S. et al., "Mannan-binding lectin in human serum, cerebrospinal fluid and brain tissue and its role in Alzheimer's disease", Department of Pharmacology, University of Oxford, UK, May 11, 1998, Neuroreport, 9(7):1491-5; Jack, D. L. et al., "Activation of complement by mannose-binding lectin on isogenic mutants of *Neisseria meningitidis* serogroup B", Immunobiology Unit, Institute of Child Health, London, UK, *J Immunol*, Feb. 1, 1998,160(3):1346-53, Terai, I. et al., "Human serum mannose-binding lectin (MBL)-associated serine protease-1 (MASP-1): determination of levels in body fluids and identification of two forms in serum", Division of Clinical Pathology, Hokkaido Institute of Public Health; Sapporo, Japan, Clin. Exp. Immunol., November, 1997, 110(2):317-23; Endo, M. et al., "Glomerular deposition of mannose-binding lectin (MBL) indicates a novel mechanism of complement activation in IgA nephropathy [In Process Citation]", Second Department of Internal Medicine, Nihon University School of Medicine, Tokyo, Japan, Nephrol Dial Transplant, Aug. 13, 1998, (8):1984-90; Valdimarsson, H. et al., "Reconstitution of opsonizing activity by infusion of mannan-binding lectin (MBL) to MBL-deficient humans", Department of Immunology, University of Reykjavik, Iceland, Scand. *J. Immunol.*, August 1998, 48(2):116-23; Thiel, S. et al., "The concentration of the C-type lectin, mannan-binding protein, in human plasma increases during an acute phase response", *Clin Exp. Immunol., October* 1992, 90(1): 31-5. These peptides can be tested for their ability to inhibit the association between MBL and MASP-1 or -2 and/or C3b.

The preferred compositions of the invention include an MBL inhibitor which is an isolated binding peptide that selectively binds to a human MBL epitope and that inhibits LCP-associated complement activation. A "human MBL epitope" as used herein is a portion of MBL which when contacted with an MBL-binding peptide inhibits LCP-associated complement activation by preventing the association between MBL and the MBL ligand or MASP-1 or -2 and/or C3b. Preferably the MBL epitope is a region of the MBL which interacts with any of the three deposited monoclonal antibodies.

In another embodiment, the MBL inhibitor is an isolated MASP binding peptide. An "isolated MASP binding peptide" as used herein refers to a peptide which binds to MASP-1 or MASP-2 and prevents LCP-associated complement activation by preventing MASP-1 or MASP-2 from forming a complex with MBL on the surface of a cell thereby preventing the resulting C3b deposition associated with the MBL-MASP complex.

In another embodiment the MBL inhibitor is a mannan binding peptide. A "mannan binding peptide" as used herein is a peptide which binds to the MBL ligand on the surface of a mammalian cell, preventing its interaction with the MBL-MASP complex. The MBL inhibitors may easily be prepared or identified by those of ordinary skill in the art using routine experiments since MBL, MASP, mannan and C3b are all well known compounds which have been characterized and described extensively in the prior art.

The MBL, MASP, and mannan binding peptides of the invention can be identified using routine assays, such as the binding and LCP complement activation assays described above and elsewhere throughout this patent application.

The peptides of the invention are isolated peptides. As used herein, with respect to peptides, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

MBL binding peptides also may easily be synthesized or produced by recombinant means by those of skill in the art. Methods for preparing or identifying peptides which bind to a particular target are well known in the art. Molecular imprinting, for instance, may be used for the de novo construction of macromolecular structures such as peptides which bind to a particular molecule. See for example Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, *Trends in Biochem. Sci.,* 19(9) January 1994; and Wulff, G., in Polymeric Reagents and Catalysts (Ford, W. T., Ed.) *ACS Symposium* Series No. 308, pp 186-230, *American Chemical Society* (1986). One method for preparing mimics of MBL binding peptides involves the steps of: (i) polymerization of functional monomers around a known MBL binding peptide or the binding region of an anti-MBL antibody (such as the deposited antibodies) (the template) that exhibits a desired activity; (ii) removal of, the template molecule; and then (iii) polymerization of a second class of monomers in the void left by the template, to provide a new molecule which exhibits one or more desired properties which are similar to that of the template. In addition to preparing peptides in this manner other MBL binding molecules which are MBL inhibitors such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include for example drug design based on structure activity relationships which require the synthesis and evaluation of a number of compounds and molecular modeling.

Peptides which bind to the MBL may also be identified by conventional screening methods such as phage display procedures (e.g., methods described in Hart, et al., *J. Biol. Chem.* 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to MBL are obtained by selecting those phages which express on their surface a ligand that binds to the MBL. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to the MBL. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to MBL any known binding assay may be employed. For example, the peptide may be immobilized on a surface and then contacted with a labeled MBL. The amount of MBL which interacts with the peptide or the amount which does not bind to the peptide may then be quantitated to determine whether the peptide binds to MBL. A surface having the deposited monoclonal antibody immobilized thereto may serve as a positive control.

Screening of peptides of the invention, also can be carried out utilizing a competition assay. If the peptide being tested competes with the deposited monoclonal antibody, as shown by a decrease in binding of the deposited monoclonal antibody, then it is likely that the peptide and the deposited monoclonal antibody bind to the same, or a closely related, epitope. Still another way to determine whether a peptide has the specificity of the deposited monoclonal antibody of the invention is to pre-incubate the deposited monoclonal antibody with MBL with which it is normally reactive, and then add the peptide being tested to determine if the peptide being tested is inhibited in its ability to bind MBL. If the peptide being tested is inhibited then, in all likelihood, it has the same, or a functionally equivalent, epitope and specificity as the deposited monoclonal antibody.

Using routine procedures known to those of ordinary skill in the art, one can determine whether a peptide which binds to MBL is useful according to the invention by determining whether the peptide is one which blocks MBL from binding to an MBL ligand. Such assays are described above and in the Examples section. Other assays will be apparent to those of skill in the art, having read the present specification, which are useful for determining whether a peptide which binds to MBL also inhibitors LCP associated complement activation.

By using the deposited monoclonal antibodies of the invention, it is now possible to produce anti-idiotypic antibodies which can be used to screen other antibodies to identify whether the antibody has the same binding specificity as the deposited monoclonal antibodies of the invention. In addition, such anti-idiotypic antibodies can be used for active immunization (Herlyn, et al., *Science*, 232:100, 1986). Such anti-idiotypic antibodies can be produced using well-known hybridoma techniques (Kohler and Milstein, *Nature*, 256:495, 1975). An anti-idiotypic antibody is an antibody which recognizes unique determinants present on the deposited monoclonal antibodies. These determinants are located in the hypervariable region of the antibody. It is this region which binds to a given epitope and, thus, is responsible for the specificity of the antibody. An anti-idiotypic antibody can be prepared by immunizing an animal with the deposited monoclonal antibodies. The immunized animal will recognize and respond to the idiotypic determinants of the immunizing deposited monoclonal antibodies and produce an antibody to these idiotypic determinants. By using the anti-idiotypic antibodies of the immunized animal, which are specific for the deposited monoclonal antibodies of the invention, it is possible to identify other clones with the same idiotype as the deposited monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Activation assays also can be used to assess the relative inhibitory concentrations of a peptide in an activation assay and to identify those peptides which inhibit activation by at least, e.g., 75%.

Other assays will be apparent to those of skill in the art, having read the present specification, which are useful for determining whether a peptide which binds to MBL also inhibits MBL activation.

In one embodiment the peptide that inhibits the activation of MBL is an antibody or a functionally active antibody fragment. Antibodies are well known to those of ordinary skill in the science of immunology. As used herein, the term "antibody" means not only intact antibody molecules but also fragments of antibody molecules retaining MBL binding ability. Such fragments are also well known in the art and are regularly employed both in vitro and in vivo. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)). As is well-known in the art, the complementarity determining regions (CDRs) of an antibody are the portions of the antibody which are largely responsible for antibody specificity. The CDR's directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical antigen specificity onto that antibody or peptide.

As discussed above the MBL inhibitors of the present invention encompass in some embodiments of the invention MBL binding peptides which include a MBL binding region which specifically binds to human MBL and inhibits LCP associated complement activation, e.g., by preventing MBL from interacting with MBL ligands. "MBL ligands" as used herein are carbohydrates or peptides with which MBL can interact. Optionally the MBL binding region is a MBL binding CDR3 region. A "MBL binding CDR3 region" as used herein is a CDR3 peptide sequence derived from the monoclonal antibodies produced by the hybridomas deposited with the ATCC under ATCC Accession No. (HB-12621), ATCC Accession No. (HB-12620), and ATCC Accession No. (HB-12619).

Three antibody producing hybridoma cell lines (3F8, 2A9, hMBL1.2) were deposited by Applicants with the ATCC on Dec. 15, 1998. Hybridoma 3F8 produces monoclonal antibody$_{(3F8)}$ having binding specificity for MBL. Monoclonal antibody $_{3F8}$ includes the CDR3$_{3F8}$ region within its sequence. As used herein "CDR3$_{(3F8)}$" includes the CDR3 region of monoclonal antibody$_{(3F8)}$. Hybridoma $_{(2A9)}$ produces monoclonal antibody$_{(2A9)}$ having binding specificity for MBL. Monoclonal antibody$_{(2A9)}$ includes the CDR3$_{(2A9)}$ region within its sequence. As used herein "CDR3$_{(2A9)}$" includes the CDR3 region of monoclonal antibody $_{2A9}$. Hybridoma(hMBL1.2) produces monoclonal antibody$_{(hMBL1.2)}$ having binding specificity for MBL. Monoclonal antibody$_{(hMBL1.2)}$ includes the CDR3$_{(hMBL1.2)}$ region within its sequence. As used herein "CDR3$_{(hMBL1.2)}$" includes the CDR3 region of monoclonal antibody$_{(hMBL1.2)}$. Each of monoclonal antibody $_{3F8}$, monoclonal antibody $_{2A9}$, and monoclonal antibody$_{(hMBL1.2)}$ specifically bind to MBL and prevent MBL from interacting with an MBL ligand.

The "MBL binding CDR3 region" refers to the CDR3$_{(3F8)}$, CDR3$_{(2A9)}$ and CDR3$_{(hMBL1.2)}$ peptide sequences. In one embodiment the peptides of the invention include functional variants of the MBL binding CDR3 region. A "functional variant" as used herein is a peptide having the sequence of the CDR3$_{(3F8)}$, CDR3$_{(2A9)}$, or CDR3$_{(hMBL1.2)}$ regions with conservative substitutions therein. As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D. Such substitutions can be made by a variety of methods known to one of ordinary skill in the art. For example, amino-acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the CDR3 region. These and other methods for altering a CDR3 region peptide will be known to those of ordinary skill in the art and may be found in references which compile such methods, e.g. Sambrook. et al., *Molecular Cloning: A Laboratory Manual,* 2nd edition, Cold Spring Harbor Laboratory Press, 1989. The activity of functionally equivalent variants of the MBL binding CDR3 region can be tested by the binding and activity assays-discussed above.

For purposes of brevity the term "ATCC deposited hybridoma" is used throughout the specification to refer to the three hybridomas deposited with the ATCC on Dec. 15, 1998. The term "deposited monoclonal antibody" is used to refer to each of the monoclonal antibodies (monoclonal antibody$_{(3F8)}$, monoclonal antibody$_{(2A9)}$, or monoclonal antibody$_{(hMBL1.2)}$ produced by the ATCC deposited hybridomas. For purposes of definiteness in the attached claims each of the hybridomas and monoclonal antibodies is specifically recited.

According to one embodiment, the peptide of the invention is an intact soluble anti-MBL monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant) of human MBL.

The peptide of the invention in one embodiment is, for example, the deposited monoclonal antibody. The preparation and use of the deposited monoclonal antibody is described more fully in the attached Examples. In another embodiment the peptide of the invention is an intact antibody having the binding characteristics of the deposited monoclonal antibody. An antibody having the binding characteristics of the deposited monoclonal antibody is one which binds to MBL and inhibits MBL from interacting with MBL ligands. One of ordinary skill in the art can easily identify antibodies having the binding characteristics of the deposited monoclonal antibody using the screening and binding assays set forth in detail below.

In one set of embodiments, the peptide useful according to the methods of the present invention is an intact humanized anti-MBL monoclonal antibody in an isolated form or in a pharmaceutical preparation. The following examples of methods for preparing humanized monoclonal antibodies that interact with MBL and inhibit LCP associated complement activation are exemplary and are provided for illustrative purposes only.

A "humanized monoclonal antibody" as used herein is a human monoclonal antibody or functionally active fragment thereof having human constant regions and a MBL binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while as retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

In preferred embodiments, the humanized antibodies of the invention are human monoclonal antibodies including at least the MBL binding CDR3 region of the deposited monoclonal antibody. As noted above, such humanized antibodies may be produced in which some or all of the FR regions of deposited monoclonal antibodies have been replaced by homologous human FR regions. In addition, the Fc portions may be replaced so as to produce IgA or IgM as well as human IgG antibodies bearing some or all of the CDRs of the deposited monoclonal antibody. Of particular importance is the inclusion of the deposited monoclonal antibody MBL binding CDR3 region and, to a lesser extent, the other CDRs and portions of the framework regions of the deposited monoclonal antibody. Such humanized antibodies will have particular clinical utility in that they will specifically recognize human MBL but will not evoke an immune response in humans against the antibody itself. In a most preferred embodiment, a murine CDR is grafted into the framework region of a human antibody to prepare the "humanized antibody." See, e.g., L. Riechmann et al., *Nature* 332, 323 (1988); M. S. Neuberger et al., *Nature* 314, 268 (1985) and EPA 0 239 400 (published Sep. 30, 1987).

In addition to the deposited monoclonal antibodies, other antibodies (e.g., anti-MBL, anti-MASP, anti-mannan-like antibodies) can be generated. The following is a description of a method for developing a monoclonal antibody specific for MBL (MASP-1 or -2, or mannan). The description is exemplary and is provided for illustrative purposes only.

Murine monoclonal antibodies may be made by any of the methods known in the art utilizing MBL as an immunogen. An example of a method for producing murine monoclonals useful according to the invention is the following: Female Balb/C mice were initially inoculated (i.p.) with 250 µl of the following mixture: 250 µl Titermax mixed with 100 µg human MBL in 250 µl PBS. The following week and for three consecutive weeks the mice were injected with 50 µg MBL in 250 µlPBS. On the 4th week the mice were injected with 25 µg MBL in 250 µl PBS and the mice were fused 4 days later.

The fusion protocol is adapted from *Current Protocols in Immunology*. The splenocytes were fused 1:1 with myelinoma fusion partner P301 from ATCC using PEG 150 at 50% w/v. The fused cells were plated at a density of $1.25 \times 10^6$/m. with 100 µl/well of a 96 well microtiter plate. The fusion media consisted of Deficient DME high glucose, Pen/Strep (50,000 U pen, 50,000 µg strep per liter), 4 mM L-glutamine, 20% fetal bovine serum, 10% thyroid enriched media, 1% OPI, 1% NEAA, 1% HAT, and 50 µM 2-mercaptoethanol. The cells were fed 100 µl/well on day one and 100/well media were exchanged on days 2, 3, 4, 7, 9, 11, and 13. The last media change before primary screening consisted of HAT substituted for the 1% HT. All subsequent feedings were done with fusion media minus the minus HT or HAT. Screening was done with human MBL plated to plastic ELISA plates (96 well plates). Purified hMBL was plated in each well at 50 µl volume containing 2 µg/ml MBL in 2% sodium carbonate buffer. The plates were then blocked with 3% BSA in PBS. Tissue culture media (50 µl) was placed in the wells and incubated for 1 hour at room temperature. The plates were washed and a secondary HRP labeled goat anti-mouse IgG antibody was used for detection. Colorimetric analysis was done with ABTS and read at a405 nm. Positive controls consisted of a polyclonal antibody to human MBL. Cells are then grown in media consisting of the following: DMEM high glucose no-I-glut, sod, pyruvate 500 ml (Irvine Scientific #9024), heat inactivated Hyclone 10%, 1% Non-essential amino acids, 4 mM L-gluamine, 100 U/ml penicillin and 100 µg/ml streptomycin. All positive wells were then screened for function in a secondary screen.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., PNAS USA, 90: 2551 (1993), Jakobovits et al., *Nature*, 362: 255-258 (1993), Bruggermann et al., *Year in Immuno.*, 7:33 (1993) and U.S. Pat. No. 5,569,825 issued to Lonberg).

An example of one method for producing human monoclonals useful according to the invention is the following: Peripheral Blood Lymphocytes (PBL) are isolated from healthy human donors using density centrifugation, and further separated into B, T and accessory (A) cells, described methods such as (Danielsson, L., Moller, S. A. & Borrebaeck, C.A.K. *Immunology* 61, 51-55 (1987)). PBL are fractionated into T and non-T cells by rosetting with 2-amino ethyl (isothiouronium bromide)-treated sheep red corpuscles, and the latter cell population is incubated on Petri dishes coated with fibronectin or autologous plasma. Non-adherent cells (B-cells) are decanted, and adherent cells (accessory cells) are removed by 10 mM EDTA. The B cells are stimulated with 50 µg *Staphylococcus aureus* Cowan I/ml and irradiated (2000R) T cells with 10 µg PWM/ml overnight. The accessory cells are stimulated with 5 IU gamma interferon/ml and 10, m indomethacin. The cell populations are cultured in supplemented RPMI 1640 which contains 10% human AB serum at a cell ratio of 2:1:0.4 (Ti:B:A) for a total of 6 days. The antigenic dose of MBL is 1 µg/ml. The culture is supplemented with recombinant IL-2 (5 U/ml) and sPWM-T (25% by vol.), produced by described methods such as (Danielsson, L., Moller, S. A. & Borrebaeck C. A. K. *Immunology* 61, 51-55 (1987)). T cells (10 cells/ml) suspended in serum-free RPMI 1640 are incubated with 2.5 mM freshly prepared Leu-OMe for 40 min at room temperature. The cells are then washed 3 times in RPMI 1640 containing 2% human antibody serum.

In one embodiment of the invention the peptide containing a MBL binding region is a functionally active antibody fragment. Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation. The terms Fab, Fc, pFc', F(ab')2 and Fv are used consistently with their standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) *Essential Immunology*, 7th Ed., (Blackwell Scientific Publications, Oxford)].

As used herein the term "functionally active antibody fragment" means a fragment of an antibody molecule including a MBL binding peptide of the invention which retains the LCP associated complement inhibitory activity of an intact antibody having the same specificity such as the deposited monoclonal antibodies. Such fragments are also well known in the art and are regularly employed both in vitro and in vivo. In particular, well-known functionally active antibody fragments include but are not limited to $F(ab')_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., *Biochemistry* 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Those skilled in the art may construct antibody fragments from various portions of intact antibodies without destroying the specificity of the antibodies for the MBL epitope.

Functionally active antibody fragments also encompass "humanized antibody fragments." As one skilled in the art will recognize, such fragments can be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

In addition to the identification of peptides from libraries etc. the peptides of the invention including those containing the MBL binding CDR3 region may easily be synthesized or produced by recombinant means. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

The sequence of the CDR regions, for instance, for use in synthesizing peptides of the invention, may be determined by methods known in the art. The heavy chain variable region is a peptide which generally ranges from 100 to 150 amino acids in length. The light chain variable region is a peptide which generally ranges from 80 to 130 amino acids in length. The CDR sequences within the heavy and light chain variable regions which include only approximately 3-25 amino acid sequences may easily be sequenced by one of ordinary skill in the art. The peptides may even be synthesized by commercial sources such as by the Scripps Protein and Nucleic Acids Core Sequencing Facility (La Jolla Calif.).

The sequences responsible for the specificity of the deposited monoclonal antibody can easily be determined by one of ordinary skill in the art so that peptides according to the invention can be prepared using recombinant DNA technology. There are entities in the United States which will perform this function commercially, such as Thomas Jefferson University and the Scripps Protein and Nucleic Acids Core Sequencing Facility (La Jolla Calif.). For example, the variable region cDNA can be prepared by polymerase chain reaction from the deposited hybridoma RNA using degenerate or non-degenerate primers (derived from the amino acid sequence). The cDNA can be subcloned to produce sufficient quantities of double stranded DNA for sequencing by conventional sequencing reactions or equipment.

Once the nucleic acid sequences of the heavy chain Fd and light chain variable domains of the deposited MBL monoclonal antibody are determined, one of ordinary skill in the art is now enabled to produce nucleic acids which encode this antibody or which encode the various antibody fragments, humanized antibodies, or peptides described above. It is contemplated that such nucleic acids will be operably joined to other nucleic acids forming a recombinant vector for cloning or for expression of the peptides of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the CDR3 region and additional variable sequences contributing to the specificity of the antibodies or parts thereof, as well as other non-specific peptide sequences and a suitable promoter either with (Whittle et al., *Protein Eng.* 1:499, 1987 and Burton et al., *Science* 266:1024-1027, 1994) or without (Marasco et al., *Proc. Natl. Acad. Sci.* (USA) 90:7889, 1993 and Duan et al., *Proc. Natl. Acad. Sci.* (USA) 91:5075-5079,1994) a signal sequence for export or secretion. Such vectors may be transformed or transfected into prokaryotic (Huse et al., *Science* 246:1275, 1989, Ward et al., *Nature* 341: 644-646, 1989; Marks et al., *J. Mol. Biol.* 222:581, 1991 and Barbas et al., *Proc. Natl. Acad. Sci.* (USA) 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for or conducive to the transcription of a nucleotide sequence which encodes a desired peptide and/or which are necessary for or conducive to the translation of the resulting transcript into the desired peptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

A preferred vector for screening peptides, but not necessarily preferred for the mass production of the peptides of the invention, is a recombinant DNA molecule containing a nucleotide sequence that codes for and is capable of expressing a fusion peptide containing, in the direction of amino- to carboxy-terminus, (1) a prokaryotic secretion signal domain, (2) a peptide of the invention, and, optionally, (3) a fusion protein domain. The vector includes DNA regulatory sequences for expressing the fusion peptide, preferably prokaryotic regulatory sequences. Such vectors can be constructed by those with skill in the art and have been described by Smith et al. (*Science* 228:1315-1317, 1985), Clackson et al. (*Nature* 352:624-628, 1991); Kang et al. (in "Methods: A Companion to Methods in Enzymology: Vol. 2", R. A. Lerner and D. R. Burton, ed. Academic Press, NY, pp 111-118,1991); Barbas et al. (*Proc. Natl. Acad. Sci.* (USA) 88:7978-7982, 1991), Roberts et al. (*Proc. Natl. Acad. Sci.* (USA) 89:2429-2433, 1992)

A fusion peptide may be useful for purification of the peptides of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion peptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. (*Nature* 381:543-546, 1988). The leader sequence of the pelB protein has previously been used as a secretion signal for fusion proteins (Better, et al., *Science* 240:1041-1043, 1988; Sastry, et al., *Proc. Natl. Acad. Sci.* (USA) 86:5728-5732, 1989; and Mullinax, et al., *Proc. Natl. Acad. Sci.* (USA) 87:8095-8099, 1990). Amino acid residue sequences for other secretion signal peptide domains from *E. coli* useful in this invention can be found in Oliver, In Neidhard, F. C. (ed.), *Escherichia coli* and *Salmonella Typhimurium*, American Society for Microbiology, Washington, D.C., 1:56-69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine, et al., *Nature* 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors:

(I) The degree of complementarity between the SD sequence and 3' end of the 16S rRNA.

(ii) The spacing and possibly the DNA sequence lying between the SD sequence and the AUG (Roberts, et al., *Proc. Natl. Acad. Sci.* (USA) 76:760., 1979a: Roberts, et al., *Proc. Natl. Acad. Sci.* (USA) 76:5596, 1979b; Guarente, et al., *Science* 209:1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra).

(iii) The nucleotide sequence following the AUG, which affects ribosome binding (Taniguchi, et al., *J. Mol. Biol.*, 118:533, 1978).

The 3' regulatory sequences define at least one termination (stop) codon in frame with and operably joined to the heterologous fusion peptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extra-chromosomally in a prokaryotic host cell, such as a bacterial host cell, transformed therewith. Such origins of replication are well known in the art. Preferred origins of replication are those that are efficient in the host organism. A preferred host cell is *E coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicons have been extensively utilized in molecular biology, are available on a variety of plasmids and are described by Sambrook. et al., *Molecular Cloning: A Laboratory Manual*, 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen, (San Diego, Calif.).

When the peptide of the invention is an antibody including both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second peptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody peptide that is produced when an insert translatable DNA sequence (insert DNA) is directionally inserted into the cassette via the sequence of nucleotides adapted for directional ligation.

The dicistronic expression vector also contains a second cassette for expressing the second antibody peptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion peptide comprising a secretion signal with a peptide coded by the insert DNA.

The peptides of the present invention may also, of course, be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the peptide. The design and selection of an appropriate eukaryotic vector is within the ability and discretion of one of ordinary skill in the art. The subsequent purification of the peptides may be accomplished by any of a variety of standard means known in the art.

In another embodiment, the present invention provides host cells, both prokaryotic and eukaryotic, transformed or transfected with, and therefore including, the vectors of the present invention.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional peptide, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired peptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

According to the methods of the invention, the compositions may be administered in a pharmaceutically acceptable composition. In general, pharmaceutically-acceptable carriers for monoclonal antibodies, antibody fragments, and peptides are well-known to those of ordinary skill in the art. As used herein, a pharmaceutically-acceptable carrier means a non-toxic material that does not interfere with the effectiveness of the biological activity of the active ingredients, i.e., the ability of the MBL inhibitor to inhibit LCP associated complement activation. Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. The peptides of the invention may be formulated is into preparations in solid, semi-solid, liquid or gaseous forms such as tablets, capsules, powders, granules, ointments, solutions, depositories, inhalants (e.g., aerosols) and injections, and usual ways for oral, parenteral or surgical administration. The invention also embraces locally administering the compositions of the invention, including as implants.

According to the methods of the invention the compositions can be administered by injection by gradual infusion over time or by any other medically acceptable mode. The administration may, for example, be intravenous, intraperitoneal, intramuscular, intracavity, subcutaneous or transdermal. Preparations for parenteral administration includes sterile aqueous or nonaqueous solutions, suspensions and emulsions. Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation. When the compositions of the invention are administered for the treatment of pulmonary disorders the compositions may be delivered for example by aerosol.

The compositions of the invention are administered in therapeutically effective amounts. As used herein, an "effective amount" of the inhibitor of the invention is a dosage which is sufficient to inhibit the increase in, maintain or even reduce the amount of undesireable LCP associated complement activation. The effective amount is sufficient to produce the desired effect of inhibiting associated cellular injury until the symptoms associated with the MBL mediated disorder are ameliorated or decreased. Preferably an effective amount of the peptide is an effective amount for preventing cellular injury. Generally, a therapeutically effective amount may vary with the subject's age, condition, and sex, as well as the extent of the disease in the subject and can be determined by one of skill in the art. The dosage may be adjusted by the individual physician or veterinarian in the event of any complication. A therapeutically effective amount typically will vary from about 0.01 mg/kg to about 500 mg/kg, were typically from about 0.1 mg/kg to about 200 mg/kg, and often from about 0.2 mg/kg to about 20 mg/kg, in one or more dose administrations daily, for one or several days (depending of course of the mode of administration and the factors discussed above). A preferred concentration of the inhibitor is a concentration which is equimolar to the concentration of MBL in the plasma of a subject. The normal plasma concentration of MBL can be assessed clinically. A normal range of MBL is 1-2 µg/ml MBL/plasma.

One of skill in the art can determine what an effective amount of an inhibitor is by screening the ability of the inhibitor to inhibit the LCP associated complement activation in an in vitro assay. The activity of the inhibitor can be defined in terms of the ability of the inhibitor to inhibit LCP associated complement activation. An exemplary assay for measuring the ability of a putative inhibitor of the invention to inhibit LCP associated complement activation is provided in the Examples and has been discussed above. The exemplary assay is predictive of the ability of an inhibitor to inhibit LCP associated complement activation in vivo and, hence, can be used to select inhibitors for therapeutic applications.

The MBL inhibitors may be administered in a physiologically acceptable carrier. The term "physiologically-acceptable" refers to a non-toxic material that is compatible with the biological systems such of a tissue or organism. The physiologically acceptable carrier must be sterile for in vivo administration. The characteristics of the carrier will depend on the route of administration. The characteristics of the carrier will depend on the route of administration.

The invention further provides detectably labeled, immobilized and toxin conjugated forms of the peptides, antibodies and fragments thereof. The antibodies may be labeled using radiolabels, fluorescent labels, enzyme labels, free radical labels, avidin-biotin labels, or bacteriophage labels, using techniques known to the art (Chard, *Laboratory Techniques in Biology, "An Introduction to Radioimmunoassay and Related Techniques,"* North Holland Publishing Company (1978).

Typical fluorescent labels include fluorescein isothiocyanate, rhodamine, phycoerythrin, phycocyanin, allophycocyanin, and fluorescamine.

Typical chemiluminescent compounds include luminol, isoluminol, aromatic acridinium esters, imidazoles, and the oxalate esters.

Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase.

The invention also includes methods for screening a subject for susceptibility to treatment with an MBL inhibitor. In one aspect, the method is accomplished by isolating a mammalian cell from a subject and detecting the presence of an MBL or an MBL ligand on a surface of the mammalian cell. The presence of the MBL indicates that the cell is susceptible to LCP-associated complement activiation, and that the subject is susceptible to treatment with an MBL inhibitor. The mammalian cell may be isolated by any method known in the art, for instance by a biopsy. Another method for accomplishing the screening assay involves the steps of contacting a mammalian cell from the subject with a labeled isolated MBL binding peptide and detecting the presence of an MBL on the surface of the mammalian cell. This assay may be performed in vitro, ex vivo, or in vivo. Many labels which can be used to observe the MBL binding peptide interacting with the mammalian cell are known in the art under each of these conditions. For instance, radioactive compounds can be used in vitro, and other biocompatible labels can be used ex vivo or in vivo. Once the subjects are identified which are susceptible to treatment with an MBL inhibitor, the subjects can then be treated according to the methods of the invention.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Example 1

MBL and Complement Deposition on Human Coronary Arteries

Isolation and Purification of MBL. MBL and associated MASPs were purified from human plasma. MBL was isolated from human plasma as previously described{Tan, Chung, et al. 1996 Biochem. J. 319, 329-332}. Briefly, human plasma was mixed with 7% PEG3500 (w:v). The pellet was collected by centrifugation and resuspended in TBS-$Ca^{2+}$ [50 mM Tris, 150 mM NaCl, 0.05% Tween 20 and 20 mM $CaCl_2$ at pH 7.8]. The supernatant was applied to a mannan-Sepharose column (25 ml, Sigma). The column was washed with TBS-$Ca^{2+}$ with 109 mM EDTA]. The protein containing supernatant was calcified to 40 mM calcium and then applied to a maltose-Sepharose column (5 ml). The column was washed with TBS-$Ca^{2+}$ and then eluted with TBS-$Ca^{2+}$ containing 100 mM N-acetylglucosamine. Western analysis and SDS-PAGE established purity for MBL, and the absence of IgG and IgM. Purified MBL and associated MASPs were analyzed by SDS/PAGE. Western blotting was performed to rule out IgG and/or IgM contamination.

Production of Anti-Human MBL Antibodies. Purified human MBL was used to immunize rabbits to produce polyclonal anti-human MBL antibodies (Harlow E, et al., *Antibodies: A laboratory manual.* Cold Spring Harbor, N.Y., Cold Spring Harbor Laboratory, 1988). Adult rabbits were injected with 100 μg of MBL emulsified in complete Freund's adjuvant. Booster immunizations (100 μg of MBL in incomplete Freund's adjuvant) were started 4 wk after the priming immunization and continued at 4 wk intervals. Polyclonal IgG anti-human MBL antibody (R2.2) was purified from sera by protein G affinity chromatography.

Human Coronary Artery Immunohistochemistry. Immunohistochemical analysis of MBL, C3d, IgG, IgM, transferrin, and haptoglobin deposition was performed on tissue specimens from normal (n=14) and atherosclerotic human epicardial coronary arteries (n=18) obtained at autopsy (Department of Pathology, University of Helsinki, Finland) from patients who expired secondary to an acute myocardial infarction (MI). The control specimens were histologically normal coronary arteries obtained from patients who died from non-cardiovascular causes. The mean (±SD) MI age (time difference between the beginning of the clinical episode and death) was 5±5 days. The mean (±SD) age of patients suffering from acute MI was 65±15 years compared to 66±24 years for the control patients. Infarcted myocardium was identified macroscopically at autopsy by discolor, pallor, and hyperemia. To improve macroscopic diagnosis, a slice of non-fixed myocardium was incubated in nitroblue tetrazolium solution that leaves the damaged myocardium unstained. Histopathological first signs of infarction were wavy myocardial fibers and myocytolysis followed by signs of coagulation necrosis (i.e., edema, hemorrhage, neutrophil infiltration and pyknosis of nuclei). Infarcts older than 24 hr showed signs of total coagulative necrosis with loss of nuclei and striations together with heavy interstitial neutrophil infiltration. Coronary blood vessel samples for indirect immunofluorescence (IFL) microscopy were snap frozen in liquid nitrogen and stored at −80° C. until analyzed. Frozen sections (4 μm) were air dried and fixed in -20° C. acetone for 10 min. The tissue samples were then incubated for 30 min at 22° C. with either polyclonal rabbit anti-human C3d (Dakopatts, Glostrup, Denmark), MBL (polyclonal R2.2), IgG, IgM, transferrin, or haptoglobin antibody (all from Behringwerke AG, Germany). After washing with PBS, the specimens were then stained with an appropriate fluorescein isothiocyanate (FITC)-conjugated secondary antibody. Controls consisted of specimens incubated with nonimmune sera or the secondary antibody alone. The slides were then mounted with Mowiol and examined with an Olympus Standard microscope equipped with a filter specific for FITC-fluorescence.

Results. Atherosclerotic coronary arteries obtained from patients suffering from acute MI demonstrated specific MBL and C3d deposits on the endothelium, intima, and media Immunohistochemical analysis of human coronary arteries, and in particular, the IFL microscopical demonstration of MBL and C3d deposition in an atherosclerotic human coronary artery was performed. MBL and C3d were observed co-localized within the atherosclerotic lesion. MBL staining of a normal coronary artery was also performed. Antisera against human transferrin, haptoglobin, IgG, and IgM did not stain normal or atherosclerotic human coronary arteries.

Additionally, MBL was observed to co-localize with C3d, with staining intensity being greatest in ruptured atherosclerotic plaques. Specifically, MBL and C3d deposition appeared to be greatest in the lipid core and surrounding areas of this core in atherosclerotic lesions. No MBL deposits were seen on normal coronary arteries, although the basement membrane sometimes appeared to stain lightly for MBL. Further, antisera against human transferrin, haptoglobin, IgG, and IgM did not stain normal human coronary arteries or atherosclerotic lesions in vessels obtained from acute MI patients. Similarly, no staining was observed in control experiments in which human coronaries were stained with non-immune rabbit serum or with the secondary antibody only. These data demonstrated that MBL co-localized with complement in human coronary atherosclerotic lesions in patients who have died of acute MI.

Example 2

Endothelial Hypokia/Reoxygenation Effects MBL Deposition

Cell Culture. Human umbilical vein endothelial cells (HUVECs) were harvested with 0.1% collagenase (Worthington Biochemical Corp., Freehold, N.J.) and suspended in Media 199 containing 20% heat-inactivated bovine calf serum (Gibco Life Technologies Inc., Grand Island, N.Y.). The cells were initially seeded in either 75 cm$^2$ flasks or 100 mm Petri dishes (Corning Costar, Cambridge, Mass.), and incubated at 37° C. in 95% air and 5% $CO_2$. When confluent, the endothelial cells were passaged with 0.5% trypsin-EDTA. Endothelial cell purity was assessed by phase microscopic "cobblestone appearance", uptake of fluorescent acetylated low-density lipoprotein and the presence of von Willebrand factor. All experiments were conducted on HUVECs during passages 1-3.

MBL-depleted Human Serum (HS). HS was depleted of MBL by affinity chromatography using mannan cross-linked to 4% beaded agarose (Sigma Chemical Co., St. Louis, Mo.). All operations were performed at 4° C. HS was treated with 2 mmol/L ethylenediamine tetraacetate (EDTA) and phenylmethanesulfonyl fluoride (PMSF) to inhibit complement activation and was applied to a mannan column equilibrated with loading buffer (1.25 mmol/L NaCl, 10 mmol/L imidazole, 20 mmol/L $CaCl_2$, pH 7.8). The resultant eluent was dialyzed overnight in Hank's buffered salt solution containing $Mg^{2+}$ and $Ca^{2+}$.

Flow Cytomeiry. HUVECs were grown to confluence in 100-mm Petri dishes coated with gelatin. MBL deposition was measured by flow cytometry in normoxic HUVECs and HUVECs subjected to 24 hr of hypoxia followed by 3 hr of reoxygenation in the presence of 30% HS. After washing the cells in $Ca^{2+}$ free or sufficient buffer, the cells were fixed, scraped, and then incubated with 20 µg/ml of monoclonal anti-human MBL antibody (Biodesign, Kennebunk, Me., clone #131-1) or isotype control monoclonal antibody to porcine C5a for 1.5 hr at 4° C. The cells were then washed and incubated with a FITC-conjugated goat anti-mouse IgG secondary antibody for 1 hr at 4° C. MBL deposition on HUVECs was measured by florescence activated cell sorting (FACS) using the FACSort flow cytometer (Becton Dickinson, San Jose, Calif.). All flow cytometry experiments were performed in triplicate.

Enzyme-Linked Immunoabsorbent Assay (ELISA) Experiments. C3 and MBL specific cell surface ELISAs were developed using peroxidase-conjugated polyclonal goat anti-human C3 antibody (Cappel, West Chester, Pa.) and monoclonal anti-human MBL antibody (Biodesign, Kennebunk, Me., clone #131-1), respectively. HUVECs were grown to confluence on 0.1% gelatinized 96-well plastic plates (Corning Costar, Cambridge, Mass.). The plates were then subjected to 0 (normoxia) or 24 hr of hypoxia. Hypoxic stress was maintained using a humidified sealed chamber (Coy Laboratory Products, Inc., Grass Lake, Mich.) at 37° C. gassed with 1% $O_2$, 5% $CO_2$, balance $N_2$ (Collard C D, et al., "Reoxygenation of hypoxic human umbilical vein endothelial cells activates the classical complement pathway", Circulation 1997;96:326-333). Following the specified period of normoxia or hypoxia, the cell media were aspirated and 100 µl of one of the following was added to each well: 1) 30% HS, 2) Hank's balanced salt solution, 3) 30% HS+3, 30, or 300 mmol/L GluNAc, 4) 30% HS+3, 30, or 300 mmol/L D-mannose, 5) 30% HS+3, 30, 300 mmol/L L-mannose, 6) 30% MBL-depleted HS+3F8 (0, 20, 50 µg/ml)or 7) 30% MBL-depleted HS +0.6 µg/ml MBL. Additionally, 100 µl of purified MBL (3-300 ng/ml) was added to select wells to form a standard curve for quantitative analysis of MBL deposition. The cells were then reoxygenated for 3 hr at 37° C. in 95% air and 5% $CO_2$. The cells were washed and then fixed with 1% paraformaldehyde (Sigma Chemical Co., St. Louis, Mo.) for 30 min. The cells were then washed and incubated at 4° C. for 1.5 hr with 50 µl of peroxidase-conjugated polyclonal goat anti-human C3 antibody (1:1000 dilution) or monoclonal anti-human MBL antibody (1:1000 dilution). The MBL ELISA plates were then washed and incubated for 1 hr at 4° C. with 50 µl of peroxidase-conjugated polyclonal goat anti-mouse IgG secondary antibody (1:1000 dilution). After washing the cells, the plates were developed with 0.50 µl of ABTS (2,2'-azino-bis(3-ethylbenzthiazoline-6-sulfonic acid)), and read (Molecular Devices, Sunnyvale, Calif.) at 405 nm. Background controls for the C3 ELISA consisted of cells to which only the anti-human C3 antibody was added (i.e., no 1-IS) or cells incubated with 30% heat-inactivated HS. Background controls for the MBL ELISA consisted of cells to which only secondary antibody and an isotype control monoclonal antibody to porcine C5a were added. Background optical density was subtracted from all groups. All ELISA experiments were performed 3 times using 6 wells per experimental group. Endothelial C3 and MBL deposition on normoxic vs. hypoxic HLVECs was analyzed by two-way analysis of variance (ANOVA).

Figure 1:
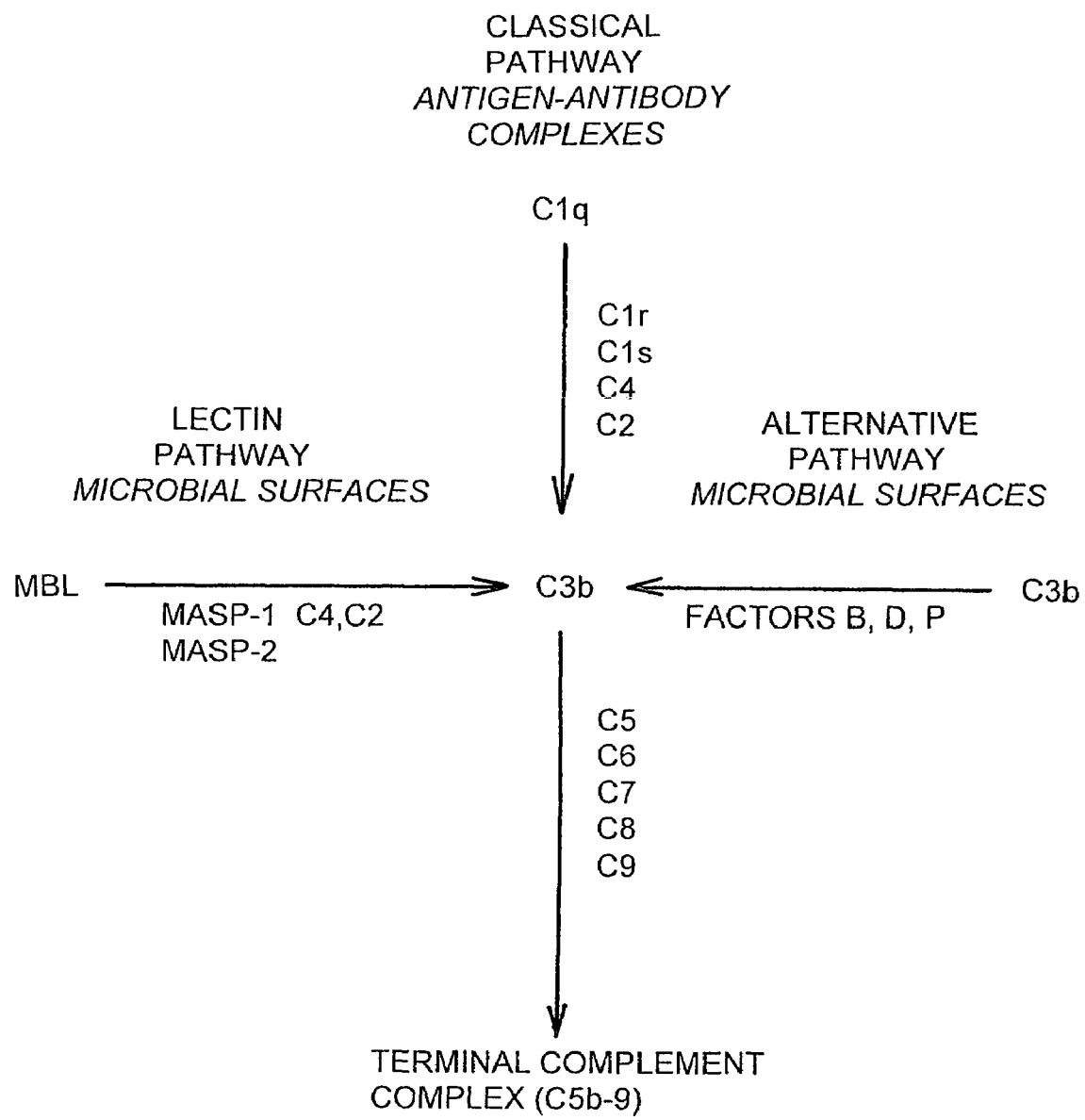
FIG. 1 is a schematic depicting the antigen/antibody-dependent classical complement pathway and the antibody-independent alternative and lectin complement pathways. All three pathways merge at C3 and lead to the formation of the terminal complement complex (C5b-9).
Figure 2:
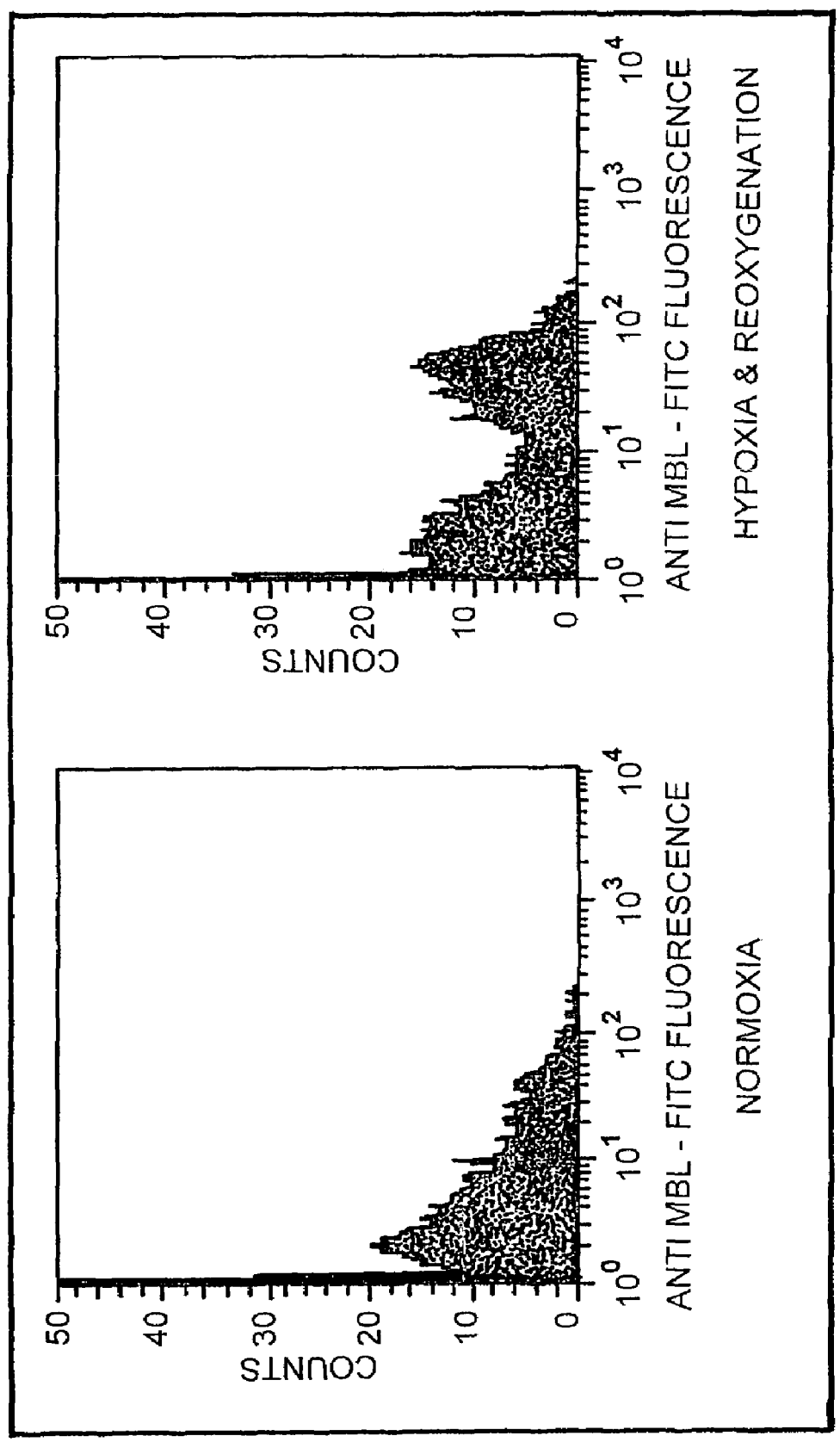
FIG. 2 depicts a flow cytometry printout to demonstrate MBL deposition on HUVECs. MBL deposition on HUVECs subjected to zero (normoxia) or 24 hours of hypoxia was studied by flow cytometry using a monoclonal anti-human MBL antibody. MBL deposition (MFI=40±3) was significantly increased on hypoxic HUVECs reoxygenated for 3 hours in 30% human serum compared to normoxic HUVECs (MFI=8±2), where MFI=mean fluorescent intensity.

Results. Flow cytometric analysis (FIG. 2) of endothelial MBL deposition revealed that the mean fluorescent intensity (MFI) of hypoxic HUVECs (24 hr) reoxygenated (3 hr) in 30% HS was significantly greater than normoxic HUVECs or hypoxic HUVECs reoxygenated in buffer alone. Further, MBL deposition was not observed following hypoxia/reoxygenation if the cells were washed in $Ca^{2+}$-free buffer. Thus, MBL deposition on hypoxic/reoxygenated HUVECs was $Ca^{2+}$-dependent.

In order to further confirm these findings, MBL deposition was measured by ELISA on normoxic HUVECs and HUVECs subjected to 24 hr of hypoxia followed by 3 hr of reoxygenation in the presence of 30% HS or 30% HS treated with 3, 30, or 300 mmol/L of N-acetyl-D-glucosamine (GluNAc) to competitively inhibit MBL deposition. MBL deposition on hypoxic HUVECs reoxygenated in 30% HS was significantly greater (approximately 3-fold increase; p<0.05) than on normoxic HUVECs or HUVECs reoxygenated in HS treated with GluNAc (FIG. 3). Addition of GluNAc to the HS significantly inhibited MBL deposition on hypoxic/reoxygenated HUVECs in a dose-dependent manner with 3, 30 and 300 mmol/L of GluNAc attenuating MBL deposition 40±4%, 71±5% and 96±3%, respectively. Finally, quantitative analysis of the standard curve formed by the addition of purified human MBL (3-300 ng/ml) revealed that approximately 3 ng or $8.3 \times 10^{-5}$ fmol of MBL maximally deposits per well (e.g., 48,200±1000 molecules/cell) of hypoxic/reoxygenated HUVECs assuming $2 \times 10^5$ HUVECs/well and a MBL MW of 600 kDa. Thus, hypoxia/reoxygenation increased endothelial MBL deposition.

Example 3

Deposition of iC3b Following Competitive Inhibition of MBL

HUVEC cell culture and quantitation of iC3b deposition by ELISA were performed as outlined in Example 2.

Results. HUVECs were subjected to 0 or 24 hr of hypoxia followed by 3 hr of reoxygenation in the presence of 30% HS or 30% HS treated with 3, 30, or 300 mmol/L GluNAc, D-mannose or L-mannose in order to inhibit MBL deposition, LCP activation and iC3b deposition. Deposition of iC3b on hypoxic HUVECs reoxygenated in 30% HS or 30% HS treated with L-mannose was significantly greater (approximately 3-fold; $OD_{405}=0.14\pm0.01$; p<0.05) than normoxic HUVECs ($OD_{405}=0.05\pm0.01$) or hypoxic HUVECs reoxygenated in HS treated with GluNAc or D-mannose (FIG. 4a). Further, D-mannose, but not L-mannose, inhibited iC3b deposition on hypoxic/reoxygenated HUVECs in dose-dependent manner with 3, 30 and 300 mmol/L of D-mannose attenuating iC3b deposition 19±2%, 52±3% and 96±2%, respectively. Thus, these data demonstrated that inhibition of MBL deposition using GluNAc or D-mannose during reoxygenation significantly attenuated complement activation and iC3b deposition following reoxygenation of hypoxic endothelial cells. Further, inhibition of iC3b deposition with mannose was stereospecific as L-mannose in concentrations up to 300 mmol/L did not inhibit iC3b deposition (FIG. 4a).

Example 4

Deposition of iC3b Following MBL Depletion and Reconstitution

HUVEC cell culture and quantitation of iC3b deposition by ELISA were carried out as in Example 2.

Results. HUVECs were subjected to 0 or 24 hr of hypoxia followed by 3 hr of reoxygenation in the presence of 30% HS, 30% MBL-depleted HS or 30% MBL-depleted HS to which MBL was added back (FIG. 4b). Deposition of iC3b on hypoxic HUVECs reoxygenated in HS was significantly greater (p<0.05) than on normoxic HUVECs. However, iC3b deposition on hypoxic HUVECs reoxygenated in MBL-depleted HS was significantly less (p<0.05) than on hypoxic HUVECs reoxygenated in HS. When MBL was added back to the MBL-depleted HS, iC3b deposition on HUVECs following 24 hr of hypoxia and 3 hr of reoxygenation was restored. These data demonstrated that reoxygenation of hypoxic human endothelial cells activated the LCP leading to increased deposition of iC3b.

Example 5

Complement Hemolytic Assay ($CH_{50}$) of MBL-Depleted HS

Methods. Hemolytic assays were completed as previously described by us {Amsterdam, Stahl, et al., Limitation of reperfusion injury by a monoclonal antibody to C5a during myocardial infarction in pigs, Am. J. Physiol. Heart Circ. Physiol. 1995; 268:H448-H457} {Lennon, Collard, et al., Complement-induced endothelial dysfunction in rabbits: mechanisms, recovery, and gender differences, Am. J. Physiol. Heart Circ. Physiol., 1996; 270:H1924-H1932} {Vakeva, Agah, et al. Myocardial infarction and apoptosis after myocardial ischemia and reperfusion. Role of the terminal complement components and inhibition by anti-C5 therapy., Circulation 1998; 97:2259-2267□. Briefly, chicken red blood cells were sensitized with sheep anti-chicken antibodies. Serial dilutions of sera were then used to lyse the cells. Hemolytic activity was calculated by using 0.1% Triton X100 and PBS as positive and negative controls, respectively. Optical density was read at 550 nm on a plate reader. Percent hemolytic activity was calculated as follows:

(Sample $OD$–$PBS$)/(Triton $OD$–$PBS$)×100=% hemolytic $OD$

Samples were run in triplicate and at three determinations per group were performed.

Results. Complement hemolytic assay ($CH_{50}$) was performed on the MBL-depleted HS in order to demonstrate that MBL depletion did not alter the classical complement pathway. $CH_{50}$ of the MBL-depleted HS revealed classical complement pathway activity similar to that of complete HS (FIG. 5). Similar findings were observed when antibodies 3F8, and 2A9 were used. Thus, the decrease in iC3b deposition on hypoxic HUVECs reoxygenated in MBL-depleted serum was not a result of altered classical pathway complement components (i.e., C1q, C1r, and C1s).

Example 6

Western Blot Analysis of C3 Activation Following Hypoxia/Reoxygenation Using Purified C2, C3, C4, and MBL Western Blot. HUVECs were grown to confluence in 96 well plates and then subjected to normoxia or hypoxia (24 hr). The cells were then washed with GVB+ and reoxygenated for 3 hr in the presence of 50 µl of the following complement cocktail: MBL (1.2 µg/ml), C2 (8 µg/ml), C3 (400 µg/ml), and C4 (200 µg/ml) (C2, C3, and C4 were purchased from Advanced Research Technologies; San Diego, Calif.). These complement concentrations were representative of the concentrations normally present in 30% HS. Following reoxygenation, the supernatants were collected and the protein concentration determined (BioRad, Hercules, Calif.). Five µg of total protein was then resolved by 9% SDS-PAGE under reduced conditions. The gel was then transferred to nitrocellulose, blocked, and probed for the C3 and C3b (α'-chain by western blot (Collard CD, "Reoxygenation of hypoxic human umbilical vein endothelial cells activates the classical complement pathway", Circulation 1997;96:326-333). Purified C3 and C3b (Advanced Research Technologies; San Diego, Calif.) served as internal standards for MW comparisons of the cleaved C3 a'-chain. This experiment was performed 5 times (n=5).

Results. Western blot analysis of the C3 and C3b a'-chain was performed under reduced conditions on the supernatants of normoxic and hypoxic (12 hr) HUVECs reoxygenated (3 hr) in the presence of purified C2, C3, C4, and MBL (FIG. 6). A significant increase in the C3b a'-chain band density was observed in the hypoxic/reoxygenated supernatants (Lanes 2 and 4) compared to the normoxic supernatants (Lanes 1 and 3). These results demonstrated LCP-mediated activation of C3 following endothelial hypoxic/reoxygenation independent of natural antibody or C1. Thus, complement activation following endothelial hypoxia/reoxygenation appeared to be mediated by the LCP and not the classical complement pathway.

Example 7

Microphysiometer Evaluation of HUVEC Receptor-Ligand Activation

Microphysiometry. Changes in HUVEC extracellular acidification rate (EAR) were evaluated by use of a Cytosensor microphysiometer (Molecular Devices, Sunnyvale, Calif.). HUVECs were grown to 75% confluence on gelatin-coated (1%) transwell capsules and subjected to 24 hr of hypoxia followed by 3 hr of reoxygenation. Following 30 min of equilibration in modified RPMI containing 1 mmol/L phosphate buffer (Molecular Devices, Sunnyvale, Calif.), the EARs were determined (Gronert K, et al., "Characterization of human neutrophil and endothelial cell ligand-operated extacellular acidification rate by microphysiometry: Impact of reoxygenation", *J. Pharmacol.Exp.Ther.* 1998;285:252-261). HUVECs were perfused with 300-1500 ng/ml of purified MBL (dialyzed in the modified RPMI) for 30 sec before the first rate measurement and perfusion was maintained for 40 min. As a positive control, the HUVECs were perfused with media alone for 15 min following MBL exposure and then stimulated with histamine (1 μmol/L, 15 min perfusion) to evoke extracellular acidification. Each concentration of MBL was analyzed in two independent chambers containing normoxic or hypoxic/reoxygenated HUVECs. The HUVEC response to each MBL concentration was evaluated in 3 separate experiments (n=3).

Results. Microphysiometry was performed on normoxic and hypoxic/reoxygenated HUVECs in order to determine if MBL evoked receptor-mediated changes in the endothelial EAR. Neither perfusion (40 min) of normoxic or hypoxic (12 hr)/reoxygenated (3 hr) HUVECs with purified MBL (300-1500 ng/ml) evoked a change in the EAR, whereas all cells remained responsive to the agonist histamine. Thus, MBL did not evoke receptor-mediated changes in the EAR in normoxic or hypoxic/reoxygenated HUVECs. These data indicated that MBL binding to reoxygenated HUVECs occurred via a MBL ligand and not a classical receptor.

Example 8

Preparation and Characterization of Monoclonal Antibodies to Human MBL

Female Balb/C mice were initially inoculated (i.p.) with 250 μl of the following mixture: 250 μl Titermax mixed with 100 μg human MBL in 250 μl PBS. The following week and for three consecutive weeks the mice were injected with 50 μg hMBL in 250 μlPBS. On the 4th week the mice were injected with 25 μg MBL in 250 μl PBS and the mice were fused 4 days later. The fusion protocol was adapted from *Current Protocols in Immunology*. The splenocytes were fused 1:1 with myelinoma fusion partner P301 from ATCC using PEG 150 at 50% w/v. The fused cells were plated at a density of $1.25 \times 10^6$/m. with 100 μl/well of a 96 well microtiter plate. The fusion media consisted of Deficient DME high glucose, Pen/Strep (50,000 U pen, 50,000 μg strep per liter), 4 mM L-glutamine, 20% fetal bovine serum, 10% thyroid enriched media, 1% OPI, 1% NEAA, 1% HAT, and 50 μM mercaptoethanol. The cells were fed 100 μl/well on day one and 100/well media were exchanged on days 2, 3, 4, 7, 9, 11, and 13. The last media change before primary screening consisted of HAT substituted for the 1% HT. All subsequent feedings were done with fusion media minus the minus HT or HAT. Screening was done with human MBL plated to plastic ELISA plates (96 well plates). Purified hMBL was plated in each well at 50 μl volume containing 2 μg/ml MBL in 2% sodium carbonate buffer. The plates were then blocked with 3% BSA in PBS. Tissue culture media (50 μl) was placed in the wells and incubated for 1 hour at room temperature. The plates were washed and a secondary HRP labeled goat anti-mouse IgG antibody was used for detection. Colorimetric analysis was done with ABTS and read at a405 nm. Positive controls consisted of a polyclonal antibody to human MBL. Cells are then grown in media consisting of the following: DMEM high glucose no-I-glut, sod, pyruvate 500 ml (Irvine Scientific #9024), heat inactivated Hyclone 10%, 1% Non-essential amino acids, 4 mM L-gluamine, 100 U/ml is penicillin and 100 μg/ml streptomycin. All positive wells were then screened for function in a secondary screen.

Functional Screen for Anti-MBL Antibodies.

Methods. The functional screen for inhibition of MBL function by anti-human MBL antibodies was adapted from the literature{Super, Levinsky, et al., The level of mannan-binding protein regulates the binding of complement-derived opsonins to mannanand zymosan at low serum concentrations, Clin. Exp. Immunol. 1990; 79:144-150}. Briefly, 100 μl of mcannan (0.5 mg/ml in sodium carbonate/bicarbonate buffer, pH 9.6) was added to RIA/EIA plates at 4C overnight. The plates were then washed 3 times in PBS/0.5% Tween pH 7.3, once in PBS and finally in veronal-buffered saline. Human serum is diluted to 4% in VBS containing 5 mM $Ca^{2+}$ and $Mg^{2+}$. Diluted sera and tissue culture supernatant or purified antibody (various concentrations) are then 1:1 to a mannan-coated well to yield a final volume or 100 μl at a concentration of 2% human sera. The plate is then incubated at 37C for 30 min. Positive and negative controls consist of human sera without and with 100 mM N-acetlglucosamine (GluNac). The plates are then washed four times in PBS/Tween. The plates are then incubated with an anti-human C3 polyclonal antibody coupled with HRP (1 hours at RT), washed and developed with ABTS and read at 405 nm.

Results. Antibody production and characterization. Following a primary screen sing a solid phase antibody-capture ELISA, we identified 11 clones that recognized human MBL. After limiting dilution and isotyping, we identified eight mAbs that recognized human MBL in an antibody-capture ELISA. Clones 3F8, 2A9, and hMBL1.2 were isotyped as mouse IgG1k, where as clone 1C10 was a mouse IgG2b. The other hybridomas produced IgM antibodies and were not included in this study.

Western blot analysis was used to determine that the mAbs recognized MBL. As shown in FIG. 7, antibodies 2A9 (Lane 1), hMBL1.2 (Lane 2), 1C10 (Lane 3) or 3F8 (Lane 4) recognized purified and reduced human MBL [i.e., molecular weight (MW) ~32 kD]. Thus, these antibodies are specific for human MBL. Clones hMBL1.2, 2A9 and 3F8 have been deposited at the International Despository Authority with ATCC designations of HB-12619, HB-12620 and HB-12621, respectively.

The most potent inhibitor of MBL induced complement activiation, N-acetylglucosamine (GluNAc) inhibited C3 deposition to plastic in mannan coated plates in a dose-dependent manner with an EC50 of approximately 1 nM. Similarly, 2A9 and hMBL 1.2 inhibited C3 deposition with and EC50 of approximately 30 and 50 nM, respectively. An isotype control antibody that recognizes MBL by solid phase ELISA did not inhibit MBL dependent C3 deposition. Thus, these antibodies are approximately 105-106 times more potent than GluNAc. The data represent 3 separate experiments with at least 4 observations per experiment. HUBECs were hypoxic for 24 hours and then reoxygenated in 30% human sera. iC3b deposition was then normalized to normoxic cells. An approximate 190% increase in iC3b deposition on hypoxic cells was observed following reoxygenation (FIG. 8). 3F8 attenuated iC3b deposition on hypoxic/reoxygenated HUVECs in a dose-dependent manner. These data demonstrate that specific inhibition of MBL with an antibody attenuates complement activation and iC3b deposition following hypoxia/reoxygenation of human endothelial calls. *$p<0.05$ compared to all groups; n+2.

Example 9

Complement activation and deposition following HUVEC oxidative stress. To characterize further the functional properties of these novel mAbs and to demonstrate specifically the role of MBL in complement activation following oxidative stress of human endothelial cells, we assessed MBL and C3 deposition on hypoxic human endothelial cells following reoxygenation in human sera.

Western blot analysis. To demonstrate the complement inhibitory action of these anti-human MBL mAbs, hypoxic HUVECs were reoxygenated in human sera treated with PBS (vehicle), 3F8, hMBL1.2, 2A9, or IC10 (50 μg/ml final concentration). Cell membrane bound proteins were resolved by SD9-PAGE under reduced conditions, transferred to membranes, and analyzed for human C3dg (i.e., part of the α-chain of iC3b). The α- and β-chain of iC3b were the only C3 stainable bands present on the cellular membranes. A representative C3dg band for vehicle, 3F8-, hMBL1.2-, 2A9- and 1C10-treated cells was observed. We observed a significant decrease in C3dg band intensity on cells reoxygenated in human sera treated with either 3F8, 2A9 or hMBL1.2. However, the non-functional clone, 1C10, did not decrease iC3b deposition (i.e., C3dg band intensity) on the endothelial membranes. These data further support the role of MBL-dependent complement activation following reoxygenation of hypoxic HUVECs. Further, these data confirm that clone 1C10 is an isotype control mAb that does not functionally inhibit MBL.

Confocal microscopy studies. Dual labeling for MBL and C3 deposition on normoxic and hypoxic HUVECs was performed to demonstrate co-localization of these complement components and MBL-dependent complement pathway activation. Normoxic and hypoxic HUVECs were reoxygenated in 30% HS treated with and without mAb 3F8 (5 μg/ml) or IC10 (50 μg/ml). MBL (blue), C3 (green) and nuclei (red) were then stained on the same slide and anzlyzed by immunofluorescent confocal microscopy. Small amounts of C3 and MBL staining were observed under normoxic conditions, confirming our finding of low level C3 deposition under normoxic conditions, confirming our finding of low level C3 deposition under normoxic conditions. C3 and MBL staining on hypoxic/reoxygenated HUVECs was significantly greater than normoxic HUVECs. Clone 1C10 failed to inhibit C3 or MBL deposition following oxidative stress. C3 and MBL staining was significantly decreased on hypoxic/reoxygenated HUVECs treated with mAb 3F8 (5 μg/ml) to levels below those observed under normoxic conditions (similar results were observed with mAbs hMBL1.2 or 2A9). It was observed that MBL and C3 co-localize on human endothelial cells under the conditions outlined above. These data demonstrate that functional inhibition of MBL with a mAb attenuates C3 deposition following oxidative stress of human endothelial cells.

Example 10

Methods: VCAM-1 ELISA. Briefly, HUVECs were grown to confluence on 0.1% gelatinized 96-well plastic plates and then subjected to 0 or 12 hr of hypoxia. The cell media was then aspirated and HBSS, 30% HS or 30% HS treated with 3F8 (5 μg/ml) was added to each well. The cells were then reoxygenated for 3 hr at 37° C. in 95% air and 5% $CO_2$. The cells were washed, fixed, washed again, and incubated at 4° C. for 1.5 hr with the anti-human VCAM-1 mAb (clone 6G10 obtained from the Developmental Studies Hybridoma Bank, University of Iowa, Iowa City, Iowa). A peroxidase-conjugated goat anti-mouse secondary antibody (Cappel, West Chester, Pa.) was then used. An inappropriate isotype control antibody (mAb GS I to porcine C5a) was used to assess background optical density and fluorescence was subtracted from the data. These experiments (6 wells per experimental group) were performed 3 times (n=3).

Results: Inhibition of VCAM-1 expression following oxidative stress. We have demonstrated that oxidative stress of HUVECs activates complement and results in C5b-9 dependent VCAM-1 induction. Thus, we examined VCAM-1 expression by ELISA to demonstrate further the functional significance of MBL inhibition. As shown in FIG. 9 and confirming our own findings, reoxygenation of hypoxic HUVECs in 30% HS treated with PBS (vehicle) resulted in a significant increase in VCAM-1 protein expression. Treatment of 30% HS with 3F8 (5 μg/ml) significantly attenuated VCAM-1 expression. Since VCAM-1 expression in this model is mediated by C5b-9, these data demonstrated that C5b-9 formation is dependent on MBL deposition and lectin pathway activation.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

Deposits: Hybridoma 3F8, 2A9, and hMBL1.2 were deposited on Dec. 4, 1998 with the American Type Culture Collection (ATCC) as ATCC Accession Nos. HB-12621, HB-12620, and HB-12619, respectively, under the terms of the Budapest Treaty.

The ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R §1.14 and 35 U.S.C §122. The deposited material will be maintained with all the care necessary to keep it viable and uncontaminated for a period of at least five (5) years after the most recent request for the furnishing of a sample of the deposited hybridomas, and in any case, for a period of at least thirty (30) years after the date of deposit or for the enforceable life of the patent, whichever period is longer. Applicants acknowledge its duty to replace the deposit should the depository be unable to furnish a sample when requested due to the condition of the deposit.

We claim:

1. A monoclonal antibody or fragment thereof that binds to human mannose binding lectin (MBL), wherein the monoclonal antibody is produced by hybridoma cell line 3F8 deposited under ATCC Accession No. HB-12621.

2. A monoclonal antibody or fragment thereof that binds to human mannose binding lectin (MBL), wherein the monoclonal antibody is produced by hybridoma cell line 2A9 deposited under ATCC Accession No. HB-12620.

3. A monoclonal antibody or fragment thereof that binds to human mannose binding lectin (MBL), wherein the monoclonal antibody is produced by hybridoma cell line hMBL1.2 deposited under ATCC Accession No. HB-12619.

4. A hybridoma cell line 3F8 deposited under ATCC Accession No. HB-12621.

5. A hybridoma cell line 2A9 deposited under ATCC Accession No. HB-12620.

6. A hybridoma cell line hMBL1.2 deposited under ATCC Accession No. HB-12619.

7. A composition comprising:
an antibody or fragment thereof that binds to human MBL, wherein the antibody is produced by hybridoma cell line 3F8 deposited under ATCC Accession No. HB-12621, hybridoma cell line 2A9 deposited under ATCC Accession No. HB-12620 or hybridoma cell line hMBL1.2 deposited under ATCC Accession No. HB-12619, and a pharmaceutically acceptable carrier.

8. The composition of claim 7, wherein the fragment is an $F(ab')_2$ fragment, an Fab fragment, an Fv fragment or an Fd fragment.

9. An antibody or fragment thereof that binds to human MBL, wherein the antibody is produced by hybridoma cell line 3F8 deposited under ATCC Accession No. HB-12621, hybridoma cell line 2A9 deposited under ATCC Accession No. HB-12620, or hybridoma cell line hMBL1.2 deposited under ATCC Accession No. HB-12619.

* * * * *